United States Patent
Yoon et al.

(10) Patent No.: US 11,020,442 B2
(45) Date of Patent: Jun. 1, 2021

(54) **VIBRIO PARAHAEMOLYTICUS BACTERIOPHAGE VIB-PAP-2 AND USE THEREOF FOR INHIBITING PROLIFERATION OF *VIBRIO PARAHAEMOLYTICUS***

(71) Applicant: INTRON BIOTECHNOLOGY, INC., Gyeonggi-do (KR)

(72) Inventors: Seong Jun Yoon, Seoul (KR); Soo Youn Jun, Seoul (KR); An Sung Kwon, Gyeonggi-do (KR); Soon Hye Hwang, Seoul (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 363 days.

(21) Appl. No.: 16/064,725

(22) PCT Filed: Nov. 10, 2016

(86) PCT No.: PCT/KR2016/012905
§ 371 (c)(1),
(2) Date: Jun. 21, 2018

(87) PCT Pub. No.: WO2017/111305
PCT Pub. Date: Jun. 29, 2017

(65) Prior Publication Data
US 2019/0000897 A1    Jan. 3, 2019

(30) Foreign Application Priority Data
Dec. 21, 2015    (KR) ........................ 10-2015-0182592

(51) Int. Cl.
A61K 35/76        (2015.01)
A61Q 19/10        (2006.01)
(Continued)

(52) U.S. Cl.
CPC ............ *A61K 35/76* (2013.01); *A23K 20/195* (2016.05); *A23K 30/20* (2016.05); *A23K 50/80* (2016.05);
(Continued)

(58) Field of Classification Search
CPC .......... A61K 35/76; A23K 50/80; C12N 7/00; C12N 2795/10221; C12N 2795/10232
See application file for complete search history.

(56) References Cited

FOREIGN PATENT DOCUMENTS

KR    10-2013-0021677 A    3/2013
KR        10-1267616 B1    5/2013
(Continued)

OTHER PUBLICATIONS

Bastias, R. et al., A New Group of Cosmopolitan Bacteriophages Induce a Carrier State in the Pandemic Strain of *Vibrio paraharmolyticus*. Environ Microbiol. 2010; 12(4):990-1000.
(Continued)

*Primary Examiner* — Allison M Fox
*Assistant Examiner* — Qing Xu
(74) *Attorney, Agent, or Firm* — Ballard Spahr LLP

(57) ABSTRACT

The present invention relates to: Podoviridae bacteriophage Vib-PAP-2 (accession number KCTC 12910BP) which has the capability to specifically destroy *Vibrio parahaemolyticus*, is characterized by having a genome represented by SEQ ID NO: 1, and is isolated from nature; and a method for preventing and treating *Vibrio parahaemolyticus* infections, using a composition containing bacteriophage Vib-PAP-2 as an active ingredient.

2 Claims, 2 Drawing Sheets
Specification includes a Sequence Listing.

(51) Int. Cl.
    *C12N 7/00*           (2006.01)
    *A23K 20/195*        (2016.01)
    *A23K 30/20*         (2016.01)
    *A23K 50/80*         (2016.01)

(52) U.S. Cl.
    CPC .............. *A61Q 19/10* (2013.01); *C12N 7/00* (2013.01); *C12N 2795/10221* (2013.01); *C12N 2795/10232* (2013.01)

(56) References Cited

FOREIGN PATENT DOCUMENTS

KR    10-2014-0000541 A    1/2014
KR    10-2015-0024115 A    3/2015

OTHER PUBLICATIONS

NCBI, Genbank Accession No. FJ896200.1. 2010 (21 pages).
International Search Report dated Feb. 20, 2017 by the International Searching Authority for Patent Application No. PCT/KR2016/012905, which was filed on Nov. 10, 2016 and published as WO 2017/111305 on Jun. 29, 2017 (Inventor—Yoon et al.; Applicant—Intron Biotechnology, Inc.) (Original—4 pages; Translation—2 pages).
International Search Report dated Jan. 13, 2017 by the International Searching Authority for Patent Application No. PCT/KR2016/012904, which was filed on Nov. 10, 2016 and published as WO 2017/111304 on Jun. 29, 2017 (Inventor—Yoon et al.; Applicant—Intron Biotechnology, Inc.) (Original—4 pages; Translation: 2 pages).

[FIG. 1]
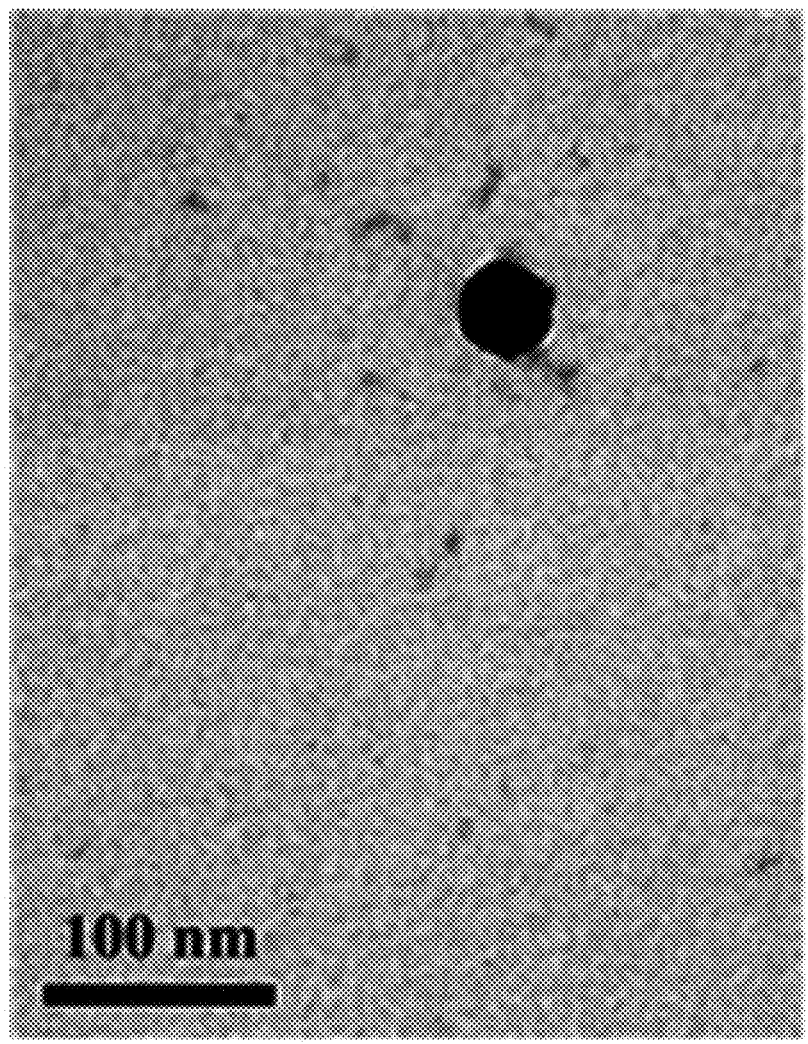

[FIG. 2]
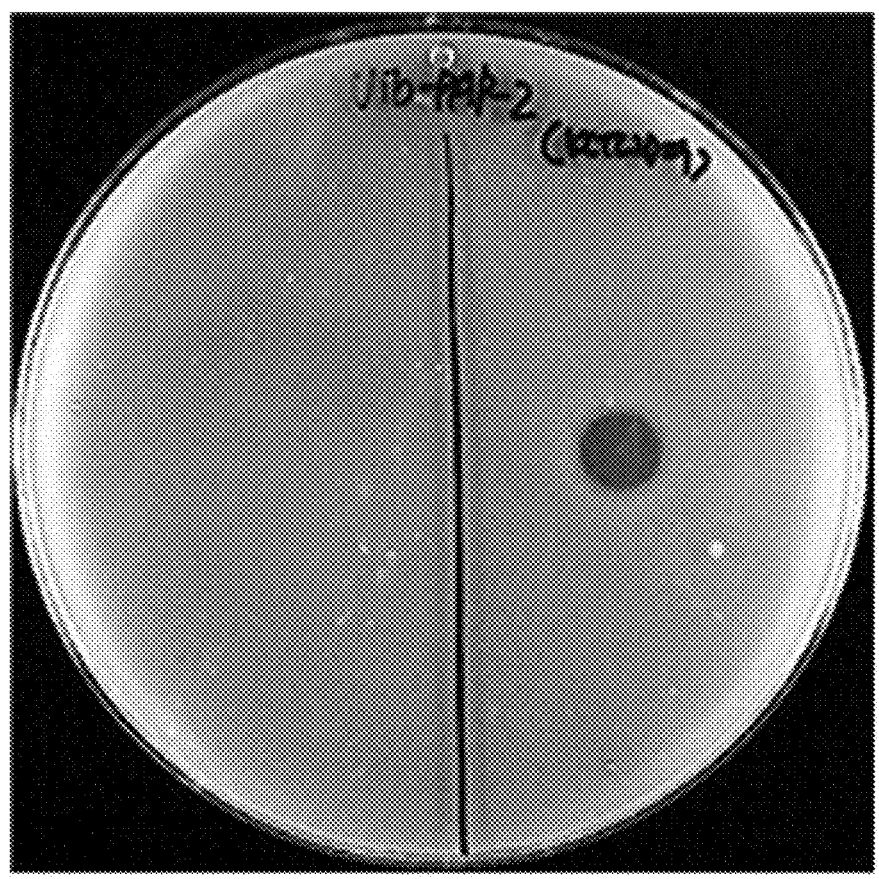

SEQUENCE LISTING

<160> NUMBER OF SEQ ID NOS: 1

<210> SEQ ID NO 1
<211> LENGTH: 43221
<212> TYPE: DNA

<213> ORGANISM: Vibrio parahaemolyticus
<220> FEATURE:
<221> NAME/KEY: misc_feature
<222> LOCATION: (1)..(43221)
<223> OTHER INFORMATION: Pasteurella Multocida bacteriophage Pas-MUP-1

<400> SEQUENCE: 1

| | | | | | |
|---|---|---|---|---|---|
| gtcattaccc | agttgagcaa | tgatttcacg | catcttatct | gtgtctgaga | tacggaagaa | 60 |
| gctcatccca | gttgggaaaa | gcgtccgtgt | cagtttacta | gcaaggttgt | taaccaacat | 120 |
| agcaccgtga | gattggaagt | cgcgttgaag | tgatacgcgc | tctccgtctt | tgttctcacg | 180 |
| tgtaaaaacg | gtaggcactg | tccagaaagc | ataacgctct | gaactcagag | taacctcaga | 240 |
| gtcctcatac | ttagcgaaca | gagcctcgtg | agtctcttga | gtatgcatac | agtaccttat | 300 |
| aatcctaagc | ttgaactaac | gtcagccatc | ttgcgtttac | gagttgtaag | accaagagca | 360 |
| tcatcggctg | ctagatttgc | agaaccgcct | gtctcaacct | taactacgtc | gtcaagagct | 420 |
| ttgttagctt | ggagtgtgtt | agcttcacgc | attcgagtct | gttcggcttc | gaactgtttc | 480 |
| ttctgcgcat | cagcttggcg | gcgtgcttct | cgtgccgcat | ctttaccact | atcgaatccc | 540 |
| atgtttcacc | ttgtagtact | tgagtctgta | ctcgtactcg | ccctgcttgt | gagggatgag | 600 |
| cacccagtcc | agacgttgtg | ccttggcata | gcgcataatc | gcacggtaca | tgtgatgtcc | 660 |
| gatattgtgg | ttcgggagca | cgtagcttaa | tacaacgccc | acgcctttac | cactgatatg | 720 |
| cggtgtcgtg | tacggtgctg | ttatagcgca | gccccctatt | agaatgcctt | tgtgatggat | 780 |
| acccatacac | atgaacccat | caactgagtc | ggcaactgag | tctctaaagt | ctttagaggt | 840 |
| aatacccga | gcgaactcag | ggttgttgtg | gtacgctagg | tttgcgacaa | ctcgcgcacc | 900 |
| tagcacagcc | tttctacctg | tgtagaattc | tagagtataa | tctgacactt | cgtgtctctc | 960 |
| ctgttcgtgg | gactttaaat | tagcagaaga | agaatggtga | atctttaacc | aactccagat | 1020 |
| tcagtgtacc | cattggaggc | atctcgatac | cctcaaggtc | agcacctgct | tccaacgctg | 1080 |
| cgtcacggat | aacctcaagt | ggattctggt | gctcagtata | tagaatcacg | aactgctcac | 1140 |
| gcaacacacg | gtgcagttcg | tcaacatcac | aagcgtgagt | cgcaactgaa | tcatggattg | 1200 |
| gaatgatgtc | accgtcaaag | ttcaagatgg | tcatcataag | gtgtgagcta | tctccttggt | 1260 |
| ggatgaagtt | cggtgagata | ccggatacag | cttctggcg | gtggttacgc | tcgtagtcga | 1320 |
| agttgtacag | cacgacttgg | ttgatacccca | tactgcgcac | tttgacgcga | gtctcgtggc | 1380 |
| ggttgcagta | gcggttaatc | accagaccac | caagcaccgt | cttccactgc | aagtgatgtt | 1440 |
| ccatcggtac | tcgctgacat | acagctttga | ggtaatccat | accacgtgca | gcggctggca | 1500 |
| tggcctcatt | aatactgtca | cgcatcagcg | gtgatacgaa | cgaacacagc | ttgaacagtg | 1560 |
| tgtactcgtc | tgtaccctcg | taaccctcat | cagcagcacc | aaggaaaatg | taatccgtgc | 1620 |
| agctacgtaa | tgtggcagag | tagaagtacg | tcatcgttgg | gcgcttggtc | attgaacgtg | 1680 |
| tgatagggtt | cagtgtccag | taatgtgctt | gcacgattgt | ctcagggtca | cgtagagcag | 1740 |
| ccttgatttt | cgagtcagta | cgctgcttaa | catccatgta | caggtcggcc | ttggttaagt | 1800 |
| taccatccca | gaataggttc | gttagcttac | cgccgattgg | gtcacgtagc | attgcagaga | 1860 |
| agtgctgacc | accagagtta | gtggcatcca | aagctaccgc | aatattcgac | tcgtacttct | 1920 |
| cagggtcagg | agagtctaga | gcttcgatta | gttggatact | agccgcaagc | atacaccaga | 1980 |
| attcatctgc | gtctttgaag | tcctcattat | tcaacgggtc | tttaacccac | tcacggattg | 2040 |
| cgtcaagacg | ttcctcagtc | cacttggcac | gttcttcgaa | caatggctta | tcaaaaccaa | 2100 |
| aacatgttgc | cacttgtgct | ttcagccaga | atagaccacg | cttacctagt | ggcttcttac | 2160 |

```
gcccaagcag cagcagcgcc ttttggatgt cagagccttg tgggttcaag tgtgatttga      2220
agtacaagcg gtaacgccag tcaacacagg tcgggaagta caacgcatct tcatccatga      2280
agcggcgaca caagtcaagc gtgatagcca actgacgaat ctgtgataca cgtttacgtt      2340
cctttgtgta ccactgacgc atctgggtct tccaaacctc aaacgcctct tggtcatcct      2400
cagaccagtc agccttgtca gtaccgtgta ggtggaactt aggctgtggt ttctggtggt      2460
ggcttgggat accaacgtca aagcccgtag ccttggcttg tagtactaag tcgtaaatac      2520
ttttgttcac gacgtaaggc acttcctgtg ctttgttcaa cgcttgacgg atacctgtcg      2580
cctgtttaaa cgcctcgttc acttcacgca aacgggaacg cttgatgtgt cggttcgagt      2640
acgtatggcg acggctcagg tcagttaagt aaccgccgtt gtaaatgtct tcgtgacgta      2700
ccggagggac aatcatcggt gggtagtgca ccatagtgtc ggcgtgctca agcacatccg      2760
agaacacacc ttgcagttct tcggctggct cagcgtacag caaacctttc gggccttgta      2820
cccattcaaa gataccagta tcgtgcacac actggagcaa caagcggcct acgttgaagc      2880
aggttgtgtt gtcccaaggg tcagtttcca gtttcacgtt cgcactagcg gcacggaacg      2940
tacgcaagat atgagattgg gaacgcgtct tgtgctcttt caagtattca tacactcggt      3000
tcatgtacgc aggtgcaacc acctcagcat tctgagctat gatttctgat tgcactgagc      3060
gacctagtga tgtaccgaga gattggatag acgacatccc caactcagtt gaggcaatgt      3120
tgttcagtag agtgttaat gtcatcaccg tcagaacatc cgacgacact aaacggatat       3180
agccgcgata cttagcacca acgccacgag tcttagaggc tttcagctcg tcaattcggg      3240
cgctaacacc gtcatacgcc gcattaagca gacgctgcac aggtgttaac tcagtagcac      3300
gaccattctc caaggcatcc agcacagctt tgcggctgcg ctcgattgcc tcagtcttaa      3360
atgtttcttc aatgcgctct tgacgagcgg ctttttcttc gaatgtctca cgattcttgg      3420
tgacagacat aaacactcca atacattaca acgttgtttt caaattgcgc tgaatcataa      3480
gacgcagcaa cttgcgtttc tctttgtccg taatgccgag gtacagcttc cgtgctgtac      3540
cacttctacc tgattgaatg tgtttgggcaa taactgcgta ctccctgtcc acattcacag      3600
gtgcttcatc tgcgaagatt aattccgcag acgctccacg atagttcgac atgcggcctc      3660
cggtttaccc tcaatcatca ctacgtcgag gtactcaatc gcaggatgtt tcacagttaa      3720
gtaactgcgg ctgtcgttag cgaacgtaca accacgaccg tacatacgga cgaccagtac      3780
ctcaccaccc atagggctgt gttcaatgaa gtcagctacg ctaaccgctt cctctgggaa      3840
accgcagtcg gtgaataccg gaatacgtcc gtattctagc acctcagcag cacgagcgcc      3900
agccatttgt ccgtagtagt cagcaccgaa ctcaggcttg atgatgtcct cactcacatg      3960
aataagcact tcacgtggtg acttaccacc cagttcaatt tgacctacgt ctttcgtgtt      4020
gcggtcagac gctaacgcaa taaacttagg caacgccata cccacatgct tcgcagcatc      4080
acggtacagg gcatctttca ctgctaggtt aaaggcattc atcaggtaat ggtcacgtag      4140
catttcagct agtgtgtcct taccgatacc cggtgggcca ttcagaatta aacatttaat      4200
cattgacctt tgctctccca atgtcgttgc atttgccagt aatgataagc cgtgtcaccg      4260
tccttagctt cacgactcat acgggcacac cattctgagg gttctcacc actcgccatt       4320 attcttgctc cttagaacgc gcacgcattt tacgagcggc tgcacgacgg gcacgttctt      4380
tcttcgcacg agcagcacgc ttgtcttcct cagtcttatg accgggatac attaagccag      4440
ttccctcttt ctccgtgctt tcgaggtagt ctgctaggcg acgcagagca gggatgattt      4500
```

-continued

```
gctggtaatc catttttacca acaatccaac gccctacagc gtttgcaacc ttaccctcac    4560
ctgcattgca ggaacggcaa agtgcgccac gaatctctcc tgtctcgtgg ttgtggtcta    4620
caactacagc acctttagta ctgaactgta agtcattcaa gcacaggggg caagtgcccc    4680
cttgctcagc cccaagtttg cgcccaatgg ttcgtaactg ggcgcgagta acctttcgta    4740
aagtcttaga tgaactcatt agctagtgcc tccatatcca tatcttcctt aatctggttg    4800
aacgctgact gccacatatc gcggtcagtg tcgcgcagct caatcatggt ggcttctagt    4860
tgagcacgtg tctcaggttt gctgtccttg taccacaact ctaaggcacg ctcatacaac    4920
tttactgcat ggttttttact aggcttcttc atctggatta tcctgtttat gtttgataac    4980
cgccatgtga tatgtatgca actgctccag ccagttgcga tactcaggga cagttacgac    5040
ttccataagg taggcgtatc cagaatcatc agcagaccga cgcaaccaaa gcatttcagc    5100
ctcagcgagt gggtcttggc gagaagcagc gtacttaccg acgacggcgt tagctactac    5160
tgtctcatca tctggcgaac cagtgataag gtctgttaag aattcgtagg ctttagttgg    5220
cccacacaac ttaccgtcta agcggtcaat gccacggatg ttatcggctg aatcccccat    5280
gagcatttgt gcccagaaga acgccgtacc gtgacctttg agtggcatgt tctcccctc    5340
gtaccacttc acataaccga agcgattgtc gattgtgcta gtgatagcga gtttctgctc    5400
ccagtacggg gcacgagtca tgcgcaaatc tttatcaccg gaactgataa gcccgttcgg    5460
gtacagttcc tcaccacgct gtatcatcag gtcgtcggct tcttcctcga acgcccaaat    5520
cactgagata ccatcaggat gctcatgcag tttcatgttc tgcacagctt gcttcaacat    5580
atcaagcagc ggtggcttct gcttaccttt gcggttagcc tgatacggtt tgaatgttgg    5640
atacaatgga cgcagacact taggcgagtt gctgtctgtg caatacacct cagcggtttt    5700
acagttcgag tagaacattt cctgtagaat cagggagtgg aagcgtcgaa tcgcagtcgg    5760
caatgtctta acagttgcgg ctgcttgata caagtaaaag tccccatcaa ggatgaggac    5820
ttgacctgag tcaacgatag cgaactggtc gtccaaggca tccaagttta atccatgaat    5880
gcctgtcatg attacttatc cccagtctta atgtaataca gcatgtcctt tgccatgtcc    5940
ttaaagtctc ggtacgtgtc cggtacgaac tccataataa accacgtgac aaagattaga    6000
atgagaagcg acggcaacgc taagatgaac aagagcacca tcaggattcg acatagcttg    6060
gacttgccca atagctcgat gtcaaacacc gtcttaccat gaccattcaa ccactcgtac    6120
caccaagcta caagcaccaa gtcgatacta agcgccatga agtgtccaac gctaggagca    6180
acagccatag catgaatatc ataccccaatg acggcaagta gtggtactgc agaaaccgc    6240
ttaaaagcca cgcccacatt agtactcttg aatttatcaa cgacttcatt gaacttcttc    6300
tttaaccatt taaacattac ttttccttaa tacccaaaat tagggtattt cttttcaaac    6360
tcttggcgag taagacgctc ggccttaccc acatgaatac gctcacctgt taagacgatg    6420
gtggcttcct ctccatctaa cttgagattc cagccaccgt tgataaccca cagttccccg    6480
ttggtatcgt ctgtacacag cagtggtgac gcagcatcag ggaagtaggt caacattata    6540
ggtcagcttc cttaacgaac acaccgtcgc gcatttcgcc tttgcggtct tgatttcac    6600
tgtaggcgaa gttcacacac tcatacaacg ttaggtcgta gtggtgcgca atgatgtaca    6660
gtgtacagta catacgacgt aggtgctcaa tagcaatcac agcgtctgct aatgattcct    6720
cattgtcgat gtcgtagtca tacagcgcac cgataatgtc cgacgtctga gcattcagcg    6780
taccgataat accagcgcgg ttcttctcag gggatagtgc cgctactgct tcaagttgtg    6840
ccagcatacg ggtgaagtca gaggtgttca ctacgtcttc gaagtcagca ccaagctgtg    6900
```

```
cagcaatgat gtcgagtact acgatggagt cgccgatacc atctttgagc aattcgaact   6960
tgcctttcac gatagcggta attacttcgt tcatttcttc tgacagcttg caagcctgag   7020
ccagcggtgt acagcctttc agaatgttac gagcaccagc ccactcgcgg attttaccga   7080
acaactcacg taagccctca ccgcagttgt atgctactac ttgaacttcc tgctcggcta   7140
cgttctgtgc ttgtttctca tccatttttc agttccttat cgtgggttga tgatttgatg   7200
gttggtcatg gtcttgaagt cttcaagcat aacaacgttg tcgtcgttca tgatgccaga   7260
gtactgtgcc atgtgagcgc cagcatcgcc gccgattact agcatgtagt tggtcatagc   7320
ccatgagcgg tacttctgtt taagaccacc ggacttgttg atgatgctca agcggtacac   7380
acgaggcaac actttgccac ggcggaatac cttaacggtc tgctctttgt agtccgtggt   7440
gatacgctcg atgtcggtct ggaacgaata cgctttctta atgcgttgtg caaattgagt   7500
gatgttcatt ctgtatcctc agttaagggg gcggcttgca ccgcccggtt agtgattaga   7560
ctgctggtgc gtccggcatt gttggcattg caggtgcatc aggcattgct gcttgagcgg   7620
ctgctgcatg gtctgcctgt gttggtgctg actcagcttt aggttcgtct gctggtggca   7680
ttggtaggcc accctcaagt agagcttgaa gtggtgaacc ctcgtagtcc acagctttca   7740
agatgtcttc ttgaatgaag ttcttagact tacctttatc atcagtaccg tcaatgtaca   7800
acgagtccca agtctcttta gtcgggttag accataggaa cacttggatt ttcgaagtgt   7860
caaactcagg tagcgtgata ggtgcacctg tttctgggtc gaacttagga agcggtgaca   7920
gagtttcgaa cttcatcgtg ttgtactcac gaccatcttt ctcttgcaca tccagttcca   7980
tacgaaaaca ttggttcaga ccttgagcaa ggtgcttcaa cgtaccagtg tagttcatac   8040
ggtcaaacag cttcttagcg tttgctttct cgtggttgct gactggcatc ttcaacgagc   8100
gaatgtaaac ttcttcacca ttcgggccgt agaaacagaa accaacacga acgttcagtg   8160
cagcagggcg accagttggt ttaccttggt gcgtcggtac aactttaccg tactcgatgt   8220
actcaatcat acgacagttg tatgccgctt tcggcaggac gattttctcg ccaccaccag   8280
taccagtctc ggtcatatcg actgcttgag tttcaacagc agcttctaca agtgagttca   8340
attggtctag tgggttaaat ggagtagtca ttaatattac ctcagtactg ttaggtttgt   8400
tgtctttctc cctgtacgtg actctttaaa gaggggagac tcacaggag aacggtttgt   8460 caagggtttc ttttgaaagg ctgacttagc cctgtaactt tttaattatt atttgacggg   8520
ttcacaaatc catgctaggc tcggttcacc cgccgcgagg ttccacaccc tattactctc   8580
tcaactcgtc taatttagac aggtcgtaca taacaggaat gcaatcgtac ttcacacaca   8640
attcgattat cttatcgaca cgcccagtac gcgctgtacc gagcactaga ggataaccct   8700
gtacgaatgt atcaattgtg tatagatgcc ccttaatgaa gcgcatatca tctgtccaga   8760
cacgattcaa ttcacaatca aagtcagcta ctgcttcgtt catgttaggc ttacggctga   8820
acaagacatc aatctcaatg accgatgct taatcttgat accaccatac agcttctcat   8880
cgaagtcgct gtcacagttg tctgggtcat cagtgtaggc aaggaacact tcgctggcta   8940
tatcgagctg actcagcgta acgctcatac ctaccatcca gttgaacacc tcagcggtgc   9000
atgagtcagg gccgactgcc acaacgatgt cgaggtcttt tggtttgaag cctcgtgcca   9060
tatctcgcac cgccccacca gcaaccgcca cttcatatgg gcggttgata gtagagtgaa   9120
taagctgagt gatgtcacgc gctgcaatat ctaatacatg cttattcata cgagttccta   9180
tggtagttga gggatgatag ccacagcggt tgactgtgct tcgaattctt ccggtaggta   9240
```

```
cttctcaata ccgtcccaac cgtcagtcaa ctgtttaagc gtcttgaatt gctcaagtgc    9300
ttgacggtac acacgttcct gtgcacggcg ttcttcgtgc cacttctcgc tgcgaatctc    9360
atacgtttca taagctgact tatctttgag gtacgcttga tagattggtt cgtcggtgta    9420
gagaatacaa gtaccgtttg gtacacaagt tggtactgag ttgttatctt cgtcacggaa    9480
gtaatcccag atagtgccga tgtccttacc atcacggttc ttgatataca aatgcattga    9540
tgtggatttg ttcaaagctt ccggtcttag gccgctgaat tgaatcgcct ctgcaatacc    9600
tgatttagca taccaacgct gttggaacgc cgtgatagct agacgggcag cactagactt    9660
aggtgcggct ggcttaggat tcttggtctt ccagtcatcc atgatgtttt taaggattgc    9720
agtacgtttt tctttgttca atcggatagt agccatgtta ttttcctcgt ggttcgatgg    9780
tgcttagtag gtacacagcg aggtctaatc gctgcttagg tgataggtag aatgcagtca    9840
tcttacattc ctcaagttcg tgtgtgccgt cctcggacat agcgtcatgt atctctaaca    9900
cgatgtctcc actccagtgt tggtcatggg cgattaggtg ggcacagttt gattcatggt    9960
ggataaccac acgatgccaa tcgtcagggc atcgtaagcc accagcttgt gttaacttgc   10020
cacgataagg tgggttaacg tatggttcaa caggatggtt aacgattggc ataagtacct   10080
cttagtgaat gtgtgttttg ttgtacattg atgaacccat ttccgcagca gcagggaatg   10140
gtacgtcttt caagtgaccg tagttaggcc atagttgcag gatgcggtct ttagcacgct   10200
ccatgatgtc tttcacagcc agtgcagcct cacgccccac ttcttcgttc gcagcgtcta   10260
ggtacgcagc atcgtgaacg ttagtgatta gacatacttg gttgtcgtac cagttcttag   10320
caatcatgtg gcgcagaatc ataccgaacg caaccgccat gaggaagaac gcttcgcctt   10380
gacaccagta gttagcaagc tgtgtatcct tgtagtccat gactttctcc atgccacgac   10440
catcagcacg cttaacccaa cgctcaacct gacggaagct atagcgcata ccagcagggg   10500
atgtccagta gccacggcgg tacagacgga cagaaccatc gtcagtcatc tcacgcttca   10560
agttacccgg taagttacca gtgcgctcaa cttcatcacg gattacctga cggaacttag   10620
ccgtatcagg gaacagggct gcttcgttgt ctaggaacgc ttgagcgaac tcgacagtac   10680
aaccagtagc gaatgcaata ccagcagccg acgcaccgta ctgagccgca aaactaggtg   10740
ctttgattgc agtacgcatt gacttccaca gagcgtggaa ctcgaagccc tcatcatgac   10800
agcgacggaa cacttcttcg tagtctaggt tctcttggaa cgcagacgg tagcagtgca   10860 tatcagtacc agctttaagc agctcaagta gcttcatatc gccagtatgc acaacgccca   10920
ttacaacttc cagtgcagag tagtccacct caatgatgcg accatcttcg ccaaagcgtg   10980
aggtaaacat ttctttaacg cgagacttcg cgttgccgtc cttatcttcc tcagcacgtg   11040
gtaggttctg caagttcggg ttcgatgcag acaagcgacc tgtcactgtt gcacaagtgt   11100
taagtctgtg gtggatgata ccagaaccgt caggcttctc agggataaca tactgtaaca   11160
tcccactaga tttcgtgatg ttaccgtcat cgtcgtattc atggcgcaga tagtaagtac   11220
ctgtgtcttt ctcaagcgtt gccaatcgag aaatatcact agcgaactca aagccctgct   11280
tagctagacc agccatacag tcgccacttg agctgaacac tggcgaacca tcacatagtg   11340
tgcggttctg gcggaactca ccacgctcac cgaacttgtc ttggaagtgc tcaggtagct   11400
ccgagatttt acacaagccc ggacactggt acacagcttc gccccacttc atcttgagtt   11460
cgttcgtatt ggcacggaat accttacgta agcccttgtt cttaccggac ttatagatta   11520
caacgtcggc tggacacagg ctgtacttgt cgtatgtctc aggtgtgatg taacgcaacc   11580
cgtcaacagg gtcagtccag acctctttga ctctcagcac atggtcgtgt agctggtacg   11640
```

```
catcgacctt gacatacgtt ggtttgtcat agtgtacttt cttcttgtac ttaatcgggc    11700
caccgtaaag caacgccgac atgtggaagt cagaacccca gttgaagtca atttcttcgg    11760
gcatgtcgtc cggtaggtac gttctgaggc gagtggttag ctccgcaatc tcagcttcct    11820
gcaccgcttg gttcttctga gccactggca tgttcacgta cagaccgaac cactcacaga    11880
atgcaaagct cagtaaggca tccatacgtt cccaaacgag ggggaactta ccttgttcgg    11940
caagtgtcgc acactgacca tagaagcaca gggcggtgtt tgcaacgtca ccgttcggcc    12000
ctgcgaggta ctcatgcaag aggatggggt caatctcgga ggtaaggact ccttgttccc    12060
aaagcagttt aataccatcc actttatgag ttccgccgta tttaggggct gtttcatcga    12120
gactcggata gagtgatgtc tggtcagttg caagatactc tccgtgcatg gtacagaaaa    12180 ctctacccccc acgtcgaaga aagccctcaa atgaatctcg tgcgaattgt aagaaccatg    12240
aaacttcata agcggcgtta tgtgcaacga tgagccaaca gtcttcggga atgggtagcc    12300
actcagttgt tggagcgcca acgaaagcct ctcgtgagtt gtatcggaca ctgccgacgc    12360
tgccaatttc tgtagtgccg tctggctttt tgcggtcaac acggaacccc gactcaacaa    12420
tatagttgtc tggacagtac ggactggctt tactaccgtg atattcatgg ttctcagtct    12480
ccaagtctat aaataatacg ctactcatgt tctactccat cccaagccgc ccagaacatt    12540
ccgttcgact gtacttgttc accacgtaga cactttctaa tgcccttgcg acaccaacca    12600
tccagctcag cctgtccgat actgtgatag tagtgctcgt caccagtacg aacacattta    12660
cctttgattc gaatagtgtg ggggctacga ttagcccccg ctgctggatg aaacacacgt    12720 ttcaccttttt ccattaagcc tccatagccg attctgcgaa gccacaattg aattgacacc    12780
gttgggcgtc gaacaggact tcgaactggt tcacgctcgg tctacctgat accggacact    12840
tgttcttagg tgtgctaagc cctcgcaagc cctcagtatc gttgttaagt ttacccatga    12900
acagtgccac atccagagca ccttgcacac caatcttaga ttgcttcaat gccgtcagcg    12960
gtgggtataa catgtcgtaa ccctcagcac tgaactgcat tgtaccgacc atcaggaagt    13020
cgtgctcaca agccagcgaa cgcagctcct gccacttcgc ttctaggttc tggtgttctg    13080
tctcagcagt accaccacgg atgtttgcca ccatgtcgat gattaccaca gcggggttca    13140
tttcttccac cagcgttgca atctgtggca tggtgattga gtgcgcatcc ttgacacgga    13200
tacgatgcca atcgcccacc tcggctaagt acagcggctc gaactgtccc tcgcggtgca    13260
gctcacgaat ctctgccagt gttttaccag ttgctgcttg gtagatacgt ggcacagttc    13320
gcacagccat tgattcgttc actagccaca ggataggtct gtcaccataa cgctcagggg    13380
cacacttcat ttggttagca aagtcagcag cgattgcagc cagcaatgat gtcttacctg    13440
catcaacagg tgcggcaact gccactgtat caccgccacg cagagcacgt atattatgac    13500
gaagctgacc aaagcggcgc aatttgagac cagcgccctc ttcattcgct gcaagtacgt    13560
cgtcgagtcc acggtcttcc catgaaaaca actcgttttg agtcttgaca ttatcaccga    13620
actcccgttg aagtttcttc atttcataca tcaggtcaat ttcttcacct gcttggtact    13680
tcgtgaggat gcttgccgct cgtccagaat acgccagctc atgcatcata gttacaaccc    13740
catcgacact ggaatcgtca accgcttgca cttcatgcgt cagtgctttc atggttgcca    13800
gttcttcggg tgtgctctgc gtggcccgta atgaaaccat gctattgaat gccgcaaagt    13860
ctacttcgtc gtgctctggg taagtcttcc agtaaagacc aacccaacta agcagtgcgg    13920
aagtatccgg tgctaacatg tctttaggaa cgtaaggcaa taagttgctg tagcgcgtct    13980
```

-continued

```
tgtcacacaa tgcctttacg ataactgcgt ccataatacc tctttaatct gtgtcggttc      14040
acaatctttc gggtctttgc cgtcgattgt cagggatgt acatttgcga atggtcgtag       14100
tactttctga gctttccgtg ccccgtcaac tcctgcctta tctccgtcgt accaacagag      14160
aacgttcggc ttactgccca tctgctccat aagggacgct aaaagggcgc gggcggttag      14220
agagattgta gtgccgagcg ttgatacgac cagtacgcgt cccttgaaga acaaattcgc      14280
cacgtactga acctttatcg cactcaacgt gtcctcggta agtaccacta gcgatggctg      14340
cgtacagtcg ggtttcaagt tcactaatgt ctggaagttg ctcccatatt gaacccactt      14400
cggcgttacg ttcggtgata cactccgccc aagaaccacg ttctcgaagc ggaagattat      14460
ccgccctttg ctctctgacc actctaagcg acatacgtcc tccaacatgt tcggtgatat      14520
acctttgctt gtaaggtatg aaaacacaaa gtgctgtatt tccgcgctcg tctgactaat      14580
gcataaagca tctgcgggta taggctgcat acctcgctca tgcacagtgg catcaaggca      14640
cacatatttc ttatactcct tggtagtctg cttacagcgg ttacaccaca tttcccacga      14700
ctgcggattg ttgtacaaga tagctgctgc ggtagcacca cagcagcgaa agcgtctagt      14760
ctgaccaatg gctaaacgct tacaagctct taaccacggt gcgtccatca ctgtcttacc      14820
ttttcgtcac tagacttaac acacagtgtg tactgaacat acgcagtacg gtcaaggcgc      14880
ttactctctg atacaagt cgcctcgtct tgaataggta cagcaaccgg agcactacca       14940
ccccaagtta aagcaatgat taaccaatac ataagcacct cctaagtgca gtttaagtta      15000
ctgaatagtt ttgcgcatca tacgcactag gtcatcaaga gtacgtccct catcatcaac      15060
agcgcggcga atgtctttac cgatacaacc acgcgctgtc tgattacctg caaggtacag      15120
gatactagcc gctagtagtg gatgcgtctg cacccactca agcatttcta actcgccctt      15180
agcaccgaac tcaagcagta cttcatcaat gtctgtggcg ttgtcaagac gattcaagta      15240
atcgtcaagg tcaaagtcat catcaaccca aggcacaggc ttaggtacag gacgctcacc      15300
cactggtagc tcagcccaag tctcaggctt caagcagtgc tcaagcgtat cgtagaactc      15360
attcaagttc aacgtctcgc ggtcagagtg ttcactgtag taacccacac cgatgttggt      15420
acactctggg attgtgtcaa cgaacgttgc tgagtcagtg taaatacctg ttgtgatacg      15480
agacttcgga cggtcaaagc gttcagccag agcttccacg aattcatctg aggcacagcg      15540
tccaccaatc tgagtatgga tgatgtcagt gccacggcgg tcaaagctga tacaccactt      15600
cactttctcg aacgactcag tatcatcttg gtacgctccg gttgaaccga ctcgccccac      15660
ttcttcttcg gcaaagaacc agtactgccc ttgaatgccc tgcttaatca tcataatcat      15720
aagcacaaca ccagcaccat cgtcagcacc aagacaatcc cagataccat cggcatccag      15780
tgctaagtgc ccattaagga cacatagctt tttctttcta gggatatgcg gttcatcact      15840
gtcagggata ccacccatcc ataacgggat ttgaccatca aagtcaactg tatctgtgtg      15900
gcttgtgaac atgatgtcat cacgctcacc cacttgtaca aacatgttcc catgtctgtc      15960
cgtcgagtac tcaataccct cagcatcaag cacttcggct accacttctt gcccacgtaa      16020
accgggacgt tcttcgctta ggattgctag tagtagttcg aaagcttttg tgttgtttgg      16080
gttagtcatc acgactcctt aattgtagta gttattattc ttcgtcttca cggtggtact      16140
ctaaccactc gtcaatgact ccaagttgtt ccgcatcagt tgcagtcaaa cacccacctt      16200
gcaggcggtc ttcgaacaca cgcttaccag tcgccgcaca ctcatccatg cggtcttcgt      16260
gcatcgggcc gaccagtgga cacacttcca cttcatcgtc aaggatgtac tcaccagtgt      16320
actcagagta ggtcacatca ctttggtggt ggtagtcggt gtcatggtca acccacacgt      16380
```

```
aatgacggtc acgacagtgc tcacacactt gacgttcatg gccgccctca tacacagtgc    16440
acatatcatc gtcatgagtg cggttgtcac attcgtaaca ttcttctagg ttgatttcaa    16500
tgcagccaga tgcactttgt gcttcgtatg agctagagta accatacac actctccagt     16560 actgaccttt cgcaccgtca cacagttcta cgtgttcttc gtagccgtca aggtaaggca    16620
taagtacagt gtcagtacta tttgggtacg ggatgtaacg cagctcttga ccgtcaagac    16680
agcttgagtt gtggttgtaa ccagcgttca tcaagtgccc ctcagtgtta caaccatatg    16740
agcgaacgta ctgcttatcg tcaatgttac acacagcacg accagtgatg ttaatgaaca    16800
catccttagc tgagaactct ggtgtatcca gttcgccctc actagccagt acgttgaatt    16860
cttctaccgt taactcacgt ggtgaacggt agcacacagc tagaccgagg ctattgtctt    16920
cgtggcagta cacacgcact ggacaacgct cataagggta atcagtcata cacgaacccg    16980
gcccgttctc gtacacaaag tgccagatgt ggtcatactt aggttcagcc ggaatgattg    17040
ttgtatggat tggagagttc agtgctttca ttgcttgcag tgcgtcacgg tagtcagaac    17100
cgtcagcgta caagcgtggg attggcaggt cgttaacgat aacacggatt tgcacacgtc    17160
cctcagcagt tactacagcg gtaggcttag cagtgatgtg tttcacttcg ctttcaccat    17220
cccagattag accgacaggt gtcacacctt ggttttggaa gaagcagttc caagcacgta    17280
agaagcaaac aactcgccca tcaaaattac tgatactaga cgtacctaag tgtaggtcgt    17340
agtctctgta ccagcactca tgcagcacgt gacctaaacg gatacctttg cagatactgt    17400
cagtgcctaa gaagataatg tttgcacagt attcttcgac aaaagctagt agcttaggat    17460
gcgtgtaacc taataactta gcggcgttca gtacgtaggt acttagttgg tgcacttgca    17520
tttcgtacga catttcagag tcaaagtcta accctttgcaa accagtgcct ttagcgtgga    17580
taagcgcacc gatttcacca tcacgtgcct tagcaaagat gcggtcaggt gagtcagtgc    17640
cattaacatt aggttggata ctctcataac caccatcaat tatattcaag tagttagttg    17700
cataatgtac tcgtgcaata cgttggcacg ccttgaatac ccaaccacgt tgagtgccgt    17760
caaaggcttc gaacttctca cggagtagtg tagtacgtgg tgagatagcc ttgccgccac    17820
ggttccagcc aaagttcatc caaccagcga atgagtcaaa caaccacgt tggtgatgcg     17880 ctgttaggac ttgcgtgcta taccagtcag gacatagacc agtaaacagg gcttcaattt    17940
tacggtcgtc acagctacgt tggttcgtaa tgaagtggcg cggtgcgata gtctctttac    18000
caatagccga ggttgtatca atatccgcgc cttgtggtga gttcttaccg tatcgtggca    18060
agtgttcgta caccttaccg cttgcaccga tgaagtccac attctcagag gcaacacggc    18120
tgtagaaagc gggcatcaca gtgaatcgct caacaacatt atcagcatgt tcagctagta    18180
gcttgtaacc ctctgggtcg ttaacgccga acaattggat tgcttcgaat ggttggaaaa    18240
acttagacat ttggaactcc ttacatgagt agtatcagat tagtcaagca tgtcagattg    18300
ccatgcattt gctatacgtt gggtagcctc aaacagtgca gtgaatgcct gttcttgacc    18360
gttggttagc tcagtcagta aatcgtattg accatgctct ttgagtaact tgagagtgcg    18420
cttggcgtac gtctcggaat agaaacgcac cgtgtctagt acctgagtac catcagttaa    18480
ggtgcggtga cacagcttgc gctcaagtgg taacaacttg cgcagtttag ggtgcaccag    18540
ttgcagttct tgatacgaca agcggaaaga cttttgctca ctcagcataa accagatgag    18600
tgcagttgaa tcgcgcaggg ttaacttctc accttgctca agattctttc gtatgatgcg    18660
gtggatgtga ccactgttga agttacgcgc taccatttga tagattcgca tccagttctc    18720
```

```
ctttgaacaa aacaccacgg atattgaaac gcttgcagta ggtgacaaga gacaagccca   18780
ctacacgagc acgctctgag taaatatcac gcagcgtttc ttgacgttta cgtgtgtggt   18840
tgtggtactt gtggaaagca tcttgcagtt tcaaatgctc attctttagg tactcagcgt   18900
gctcctgagc attcatgtat cccttggtta agttgccat gttaaaaccc caacgcccat    18960
ttgtagaaca gtaactcaag tgccttgagt ccccaaccga tagccactac cgctgctacc   19020
ataacgacaa gcaccgctat aaacttgaag cgttcaatgt agcggttgaa tcgttgcttt   19080
gatttactca tagtacctcc tagtacggtg tgtggttgtg tgcagcatac acacgattca   19140
catgttgcgg tgtgatgtct agcatgtcag caataacttg acttgacaca cctttctgtt   19200
tcatcttgat aagtttacgc ttactctcag cattgagctt tgaaccggag cgttttgcat   19260
tacctttgat gccattgtaa cggatagcat gactaacctc gttgtacgtc acaccgagat   19320
agtcacacag ttctttctta gagagacgcc cgtaattgtt acggacgtac tcaagttgtt   19380
tagagttcag tgccatgctt acttagcctt tggtagaatg tctttaccgt cacgagcacg   19440
tttgagcatg gtttcaactt caccgtatga caagccagcc tcagcccact gtcccaacag   19500
acgcgccatt tgacctttca acttgccttg cttctggtca agtgtcagtt cctcagactt   19560
tttcttctct gagttctcaa gccagtactg ctcaaggatt gggtagaact ctgggtacgt   19620
catttcacgg tttacaccta gtttgcccat gatttcatca gctttcttgg tgtcacgctt   19680
gtaatgacct ttgatgccct tgctaggctc agggtttacc cacttagtcg ggcacagaac   19740
acgcagagtt gcgtcaagca tagcggcatc ggtacgtgac cagttttcca tccatgcgac   19800
gttagacttc actagcgcat ggtacagtgc agagattgtc acgttgcggc gcatagtctc   19860
agctttgaca agttgagtac ggatttgttt tacagacgtt agttttggtg ctttgtttgt   19920
tgttacagtt gacatagttt agccctcatt tggcgattga tagattagta cgcagattgc   19980
attgattgac caccgtcgaa cagtgataca ttagtgagag acagcttata gcttcgcaca   20040
ttattgatat agctaacgtg acgtgctaga ccataagcct cgttgcgagt tctcgcacac   20100
acttgaaagt gtttcttttg aacacgacgt agactgtcac gatagaccac ttcaaagtgg   20160
tacacacggc gcggtctaat gaaagtcaag tagaaactct ttgacagttg ctttaaacgt   20220
ttgaacatag ttcacctcga taaaataagc ggtggaacaa gctaccctac tagcacattg   20280
cacacaaaca cccatagact ttgaccaatg gttaaaagat tgcgcttggt aggactgtta   20340
caccgcttcg tgctaggttg cacaagatta catttgatag gactcagcga acatatagtg   20400
tcagcaaata tgaatggata cactaagccc tatcaaatga ccaatgctat cgggattggt   20460
tgccgctggc tcagttgatg ccagtacatc gtaagcggaa aactgtatac ggatttcaag   20520
cctgactact ttacacttac aattcaccgg acgcagcagg tatcaattgc tttgcccgtc   20580
gtctaactct tacttttaac tctactcgct tcgctaccag atgacccctt acagcggata   20640
gacttgtgcc tatgcttgca gatggtgtct gtcactgctc tcgcttgagt gttagaccgt   20700
ttaccagatt gttaaagaac gttgccctat tgggcggaga ctcgctggct agtgccgttt   20760
gctctgcaat acctcgcaag gtttcagagt gtcccgcagg actggctagt gccttgagtc   20820
gttagctctc gctaacatgc tttccaatgt atcactaagt tgttcaacct gtcaagcatt   20880
ttgtgattca gtgtttagtc agtcggtcac gctgtaagcg gtaattccaa cactttacaa   20940
ctaagccagc aaacgccgct ttgcattgtt taaccttagc atcaaaggca cttagttgtg   21000
actcactgag tacgctattt aagctatact acctagtgat tcattgtcaa gcatattttt   21060
aaagaacgta tcaatctggc tattgccttg cggctcaagt agcggctatt actaccatta   21120
```

```
agacaacact tgttaagtgg ctgcgacttc ctgattgatt gtgagtggct agtgcctctc   21180
gacgggatta actatcccat agctagacag agaacgcaag ccctacgact agaaatgtga   21240
agcgtatcac aataaaagcg gtatatacag tggttataca gtggtctaac aatgagttat   21300
ccacagtcaa tagcctagtc tcgcaatgtt ctatccggta taatgcattt agccacccga   21360
cacggagcga ttgacacgaa gtgtcccctt atcgcgtagt gtccactagc taacattccc   21420
tattgtagcg acgagcgaa gcgaagcgag agcgacaaag cgtaaatcaa taggatagca    21480
aagagatagc agcacgatag caagtgctaa caagtggata gcaagcgagt agcgcaaggc   21540
atcacagatg ccatatgtta acaagtggat agccactaga tagccagtcg atagccctac   21600
gtgaacaggt gacaagccag tgagttaaca ggtgagcaaa aaaggcaagc gcagagcaca   21660
gccgcgccgc ccacgcaatc gcaaggcttt ccagtcgctt tccctgctt tcccacggat    21720 agcaacacgc acgcacgcgc acgcgctgga tagcccacgc atacacacgc gagcgcacgc   21780
acgccagcgc acacacacgc acccctacgg gggaaacgcg cgcgtggatg ggggagaacc   21840
ccctcgcctg agtataacat ttttcttgtg cagggttttg cactggattg ccaatggctt   21900
tcacaggctt tcccccatgt caccactggc tttccactag cttt ccactc tctacacatg   21960 gacacttcgt gtcagaggct taaccctcgt aagccgcatg gtattcagct tgcttcgttt   22020
cacttcgctc agcttcatac agcttctgct tcatcaggta cgcttcaaga ggccacactt   22080
tcttcatggc atccacctta gcccaatgtt ctccaaccgc cttgtcgaag ttctctgggt   22140
caacacaagc tgactcacct gtgacagtga agccattctc cagtgttaac acacagaacg   22200
tcagagtagt gcccggtaca accacgtact gctcagactt aacctttgac tctacgagtt   22260
cctgtgttac cttatgttca gacatccatc ttccccattg cttgtttgta tttatcagag   22320
cggtaatccc accgggcttt ctcaccgcgt gtatcaacgt gtacacccca gtcatacaga   22380
ccgacgccac cgttagggtt cagagctaaa gccgtgtcat acagcttctg agcttctgg    22440 aagttccccc ggtctttgtt cagcaagtgt aagtccgctg catcaccatg taagtgacga   22500
gagttctcag caccgcctac agctttattg tgtacagggc agcgataacc ggattcaacc   22560
tttagcggtt ctccgaagtg ttcccgtagc atttgtacca gcataagcag ggctaggtct   22620
agtttcaaag ccccacagtg ctgacacgcg aacttcacaa tcttgaaatt cgcagtgtct   22680
ttaattagca taattactcc tattgagttg gtttccgaac aatctgcatg aacccacgag   22740
ggattaatac gttagtcggc tggtcagcac tcagcttaac actgaatgta tcagcagcac   22800
ctgtcgctgt cggcaacgca tctagctgga tgattacagg actgttagca ccatctagac   22860
gcacctgact ctgtacaaca gtaggttggt cattaatgta caaagtagcc gtcacaatgc   22920
ggttctgtgt acctgcaata gtacacacga agttgaactc atgccaccaa ccagcctgtg   22980
catacgcagt gactgaacct tgtgcagcgt tgaagtccat accgtcgtct ttgtacgtgg   23040
ctgtccagtt aatcacagga gtagcggttg cactcagtga ttgctcagtt gtgttattag   23100
tcatgtctag tacgcccttg gcgtcaatga cactaaccat gatgttgtcg taaagctcac   23160
gtgccgaggc tggcacgatg aagccctcgt tgttgtcagg cattaacgac tgaatatcag   23220
ccgccagtgc acttaatttc ttgaccgtag ccattatact gtacctataa tgtttaacgg   23280
taatggtgta ttcagagagt caaataccaa ttggtacata atagccgctt gtgtcgtgtt   23340
atttgactgg tagcggttac tgttcttgac taacgtgatt gattcagtac cgatagtgat   23400
ttcaatagat gtgtaaggtt gtgcgtttcc ggtaaatgtt aaacggacaa agttcgatac   23460
```

```
accgttaaac tcaagtgcgt acactgggta cgtctctaca gtgtctggaa tcagagcacc   23520
tttcgtcggt gtaaagccaa caacacctgt agctagggat gctggtgtaa gctcatgtgt   23580
gtagctcggc ggtgtgtaac cattaccgaa accatctgac caaccatctg accacggaga   23640
gcctagtgtc ggctctgggt caggccaagg ccaacctaag ataagctcaa cttgtcccgg   23700
acgcagtgca gggtagcgtg agtacatttc ctgacggaat gcctcgcggt ctgcccataa   23760
caccgcatca aggcgtggga actgctgcac agcattagta cgcacagcag ctcgtaacca   23820
cggaataaca ggtaatcccg gaatgcgata cggaattacg atttgcatac aatctcctac   23880
attgcagcta gtttagtagc gacgttaacg gcagtctcta aaagcttacc atccccaccc   23940
actaagtaca cagcaccgac acctgctaag aagtacaaag tcttcttaac cacaggtgca   24000
acttccttaa aggtcttcaa catttctgcg gagtcttcac gcatttgctt caaactgtct   24060
gcaagttctt tctgtgtctg ttccatagcg aataaccgtc gttcgtggtc taaaaggatt   24120
tctcgtgtag atttgtcctc aaagtcctgc atgaagacag tatctttctc tgccattagc   24180
agctccttac attacttgtt tttgcgacgt aggataaagt cagcaattgt acgtagaaga   24240
ccgaaccagt cttcgcgttt aaatgagtct aatcgtttca tagtctacct cgtttacggt   24300
gtcgtgagtt cagtcgagac agtgtgcctg tacctactcc gataccagtt cgtttatgaa   24360
gtggcttgcc agctaccgat aggcggcttg cagtgccttt gttgcgtggg cgagtatcta   24420
cgccttggta agccattggg ttcagaatga actcggctac acgcatcgtg agtgctttct   24480
cagcggctga acgttcgtcc tcaactaagt gggcattcag ttcttgaacc agcatagcga   24540
tagcatctgc gcggtcatcc ttggacagac agcctttatc gtacgtgatg tcctgtaatt   24600
gcaggaacgc actgtactgc cagcgtcggt cacgtggata cgacatacag cactcgatgt   24660
ccatgtctaa tgcagacgta tggacaacta ggcggtgacg acgagtaacc ggagagatag   24720
tgtcgatgat acgacgctct ttctgcgtac tgttacgtaa gtcgcgcaca ccaatatgtg   24780
caatgtcacg ttgcgctagg gcgttctgga acagcattgt aactgtaccg tgacccatgt   24840
tgctctcgat aacgatgtcc ttaacctcga agtcctcagc taagtcaatc aagcggttca   24900
tgttttcctc agacacacca ccttggaaac cacctgtgcc gaacaagtgc acgtacgcac   24960
tagcagcacc accgattgca aaggagattt catcaccacc acaaccagca gggtcaatta   25020
ccatgatttt gtgtttgtac gggataatct cagtcccgat gctcaaagga gtgtacaagc   25080
gtgcgccaag gacaccatca tgcacctctg ggtaaagggc acgtttatcc gctgtccaac   25140
tgaacatatc cggtgcagag ttcgaatcac cagcatggat aatcatatca gacagtttga   25200
tacgcgtacg catcgcgtct gatagggttg tatccagcat gtactgcaat gcgaaaccct   25260
ctgggccgaa gtccagctct ttctctatca acgcttcctc gtcgtaacgc tgagggtcag   25320
tagtttctcc aagcgtacca tcaacgccga agccagtgcg tcgtgcgcct tgctcaatca   25380
gcatcttgat gtacgggggct aatgtgtcgc cgtacttttc ctcttggtct acagacggga   25440
tacgtccaca ccacactcgt acttcaaaac cacgcgaggg tagtgtctta tagatactgt   25500
ctttagtctg aggtgtaccc agataaagtg tatcgccgtg cgtgttgatt gccgcaaagt   25560 cttcgagat tgtcagcaag tgctcacgct gtgtttgagt cagaccgttc ttggttgtct   25620
caatatcatc ggggattagt aagtcagcac gtttaccctg tagctgagcg gttatacca   25680 cacaagccac ggatggtgct ttctctagcg gtttcaagtc acagtgaaca tcgtaaccct   25740
cgtatgaggt gcggtcgcca cgagcagggt cggcacgcag ccaacacagc aagtcccatg   25800
tctcaatcaa acggataaca agggttgcaa cctcggatgc ctgtttctca ccaccggata   25860
```

```
caattagtac acgtgtgctc tggtcttgga taagacgcca cacgctgtac agagcagcaa    25920
gcgtactctt tgcctcacca cgctgcgcac acaccatctt cttacgaggg ccgtgctgca    25980
tgtactgggc aatgtctgct tgcatgtctg ttaagtcgaa gccaaggaat cgcataccga    26040
cgtacgcgaa gtcctcaaag ttcttgaatg tgattgcgaa catcaacgcc agctcctgac    26100
gtgtgtccac tgggatgcta cgtggattct cagcaagctt tttacagcgt tgtgctaaca    26160
actttaatcg tgtaatcacc tgtacagata aacccacgat aacctcctta gttgataata    26220
cctgctaatt catcgtcacc gtcttggaga cggcctagca gttcttgttt acgtgcctca    26280
cggcgttgcg cgagttcatc ctcgaactcg tcggctagtt cacccatagc ctcgtcatct    26340
gcatcagcag aaatgttgtt atctttgagg aacttagcaa tcactgactt atcagcggct    26400
ggaagtggaa tttcttcctc acgtgattgc ttcaattcct caatcaaagc gtcagtgaat    26460
gcagcgtgca acgccgctag acgcgaacga ctagcagctt ttgccatgtt tactccttaa    26520
atacgctcta accggatgtc ggtcagaccc tcgtatttat tgtctgttgt gttacgacgc    26580
aaggctaccc gttgttgact ctgcgcaatg aaagtcaact cataggtatc gccctcgaac    26640
attgggatgt cgattacatc gttgcccggc tcgaacgtca ccaactgcaa accagcggct    26700
tgagtggaag tacgcgccac cttgattgtc atcttgtaac gagcaccttg tactaggttc    26760
aagaactgga attcaccgtt acctgagcct tgcaacttac ggtcattacg ccactccaat    26820
cggtatggtg tgatgtactg cggtgggttc ttaccagcgg ctagatatga tgttggcaac    26880
cacgttccat cggcatcttt cggcatgtca tcatcatacg gcttaggtag ctcatacggt    26940
ggtggtagct cgttgtagaa accggagaag aagttctccc acttccagtc tcgccatacg    27000
tcagcagggt atgtttcacc taactggcgc actggttcat ctgggaacgg gatgtagtgg    27060
aagtagtcaa cgtcaatcga gtcataaatg tagtcggcac tatgtccagc ccaacggttg    27120
cccggtgcgc gtggatacca aagggcaatc catagacgac ccggaatgtc agggatgtgc    27180
gtggtgttag tccatttcaa cacaccgtca acgtagaagt ccacacgttt cgcaggtagc    27240
cctgctggtg ggtctgttc gccagtatgc cagtcgaaac gaatctcgtg ccacttaccg    27300
tcactcaacg cctcatctac ccacttctca agaagtcgg tgtattcaga gaagtagttc    27360
gggtcactct ccggtaagtc ccaagtacgc aactcaccct cccaagtgtt aagacgcgct    27420
ttatcagccg agacgtcttc catatccaca gcatctttca atgcagttgg gtactcgatg    27480
tcaatctcgt ggttacgtac aatgtagtaa ccgtcgtcct cattaccttg agcgtgtaag    27540
ccctcgtcca agaagctctg ccaacgtggg tcgttctcgt agatttcctc gtagtggaat    27600
gtccacaagg ctgtcgctgc acctttccgg tacggagagc gcaacttaca gcggaaacta    27660
cccggcccta agtactcgcg tgtaaccagt gctgaaccta cctcagtctt acgaccatca    27720
ggggcagggt gtccgatacg gtcaacacca atgacatcac catcatagta cgtaccatga    27780
ccgcgtagac gtagcacacc tttcacagca tttgctacat cagagtagtc agggtaaacc    27840
tcaacgttct cacgtaccac accaccgttc agcagcgcag tttggttgcc cacaacgcca    27900
gtaccacccc attgcttatg tgcaacgagc cagttctcac gcatttcaat caagtcagag    27960
aagtcggaat acaactcagt cttgcggcta atgtcaccct tgatgcgtac tggtagcgtg    28020
ttactcacac cgtagttggt cttgtaccgg ataaagtact gaccatcagg tacgtcaggc    28080
aacgtgtaaa tacagcggcg gttatcctgc tcgtgcggcc agttcaccag agaactcgat    28140
atatcctgcc acgtgctgct gccctcagct tgaatctcaa tgttcaagta cggctgctcg    28200
```

```
tagtagcgcg gaatcacgtt ctcgttgaat gtaccgtgtg tgtcgatgta gaaacgacgg  28260
atgtcaatgt taccaatcca cgacttgtcg taaacatcag taatagggac gccagtcgtg  28320
cccacacact cagggccaca gttgaataat acactgtcaa actgtttacc ccacagcttc  28380
aatgagcacg aagctgactg ttcattcggc gtacctttat caactgtaat cgtgcagttg  28440
tggttcgcgt cctgcgttag ttgcacttga tgccaaccac tcagacttgc taattgcaca  28500
cgtgcgtaca cgtaagtact gtcgaatcga cgataataca tcaactcgcc agagcgtgat  28560
acatgcgcac caaagctaat ctgagcactc ttttggatac cagtgccttg ttctgtccaa  28620
gttacattag agccaccata cagcagccac atgcggtctt gtccatcaac gaagtcaccc  28680
aatcggaatt gcagtgacca atgttcgggt agattgcag tcgggattgt acccacgaat    28740
gcgcctacac cccagttata gccctcttga ccggggcgag taactgtgta aaggtactga  28800
gcatttgctt gtcgcagctt acacatacgg taaatgttat caatgccgta agggtttgct  28860
gtaccttgat aaccgaagtt aacatagttc tcaagcgtgt cagcaccgtt actgtaaagc  28920
ttgtattgtg agcctgtgaa gaatgggagt gggtctggga gttctttcag accatcacca  28980
aacaaggcta cgtcgccacg ataaggcgca cctgtgaagt aacgtgcatt atcaaggctc  29040
actgtgccta cagagtcagg attattgcta taggctaagt accagcggtt gttgttacca  29100
atccagcggt aaagcacttc gcggtactgg tatactgggt tatcgtcttc accgacgttc  29160
accgcaatgt actgtttgcc atttttcgtac caaacctgat tctgaccgtg gtaatgctta  29220
ggggctaaac cctctagtac atcagccata gatacctcta ctcttggtct ttatcgttag  29280
atgagttaac gaacgcgcca ttatccacat caccaatcat cacccattcc tcgtactgaa  29340
ccggaacggt gtcaggggat tgagtggaga tagtgattgg gcctcggcgg ttcgtaccct  29400
taatgttctc aattgcggtt actcggtctg caacctcttt caattggagg aacgttacag  29460
cgtctcggtt atctgtacct tgtgccatgt tgcgcactcg gtatcggtgc atatccaagt  29520
cgccatagaa atcactaatg ccagaaccct cggtcatttc ttgacttagg tacagcaatt  29580
gagtatgcgc gtcgtctaag ttagctcggg tgaactcagc accctcagag aagatatgac  29640
gtagcgcagt gcggttggta cgccgtgtaa gcgtaacctc tacccatca gctaacgggg    29700
cgttaataaa gttaatctgt gtgcgaccct gccaagtgta atctgtaccc tcgattgcag  29760
gtgtctcatc aagcgtaacg aaaatgtcac gcgtgtcaaa gaattcaatg ctgaggacga  29820
tgttggtcat agtaccgtcg ctcgtagcac gttgtacact taatgccata aagcctcttt  29880
aaaggggat tactccccca tgttgttgat aactgcacgt agcggcatga actcttgcgc    29940
gaacggaaga atcttgctca tacgttgtgt gtccatacga ccatcgctga ccatatcctg  30000
caccgctccg atgctctgcg tcacgtaacc tagtgaggtc agggagtgtc gcggagattc  30060
accaaggaat agcggtgaca gcaaagtgat accaccaata gctgacatgt tcatagcagt  30120
gttagtgatt aattcacgtg ggctttgtgc ctctttaccg tccaacgcaa gcttagcgtg  30180
agtagccata agcatgagag ggaactggta catcataagc atcgcaagac cagcgtagtc  30240
accattctgc gtgtatcggc gcagtagttt gttagtagcc gcaatcgcaa aggactggta  30300
gccaatcaca atcttaccta ccggactgaa ctgtgcaaag tgtgaagtct caccagtacg  30360
gatgttctgc atcacagagt ccatagcacg tgtcgataca atctccaact cacgttgaat  30420
ctcatacggg aacacgccag ttggattctc agcgtaagca gcacgtagct tctgtgtcaa  30480
ctcaggtgtc agaccatgct cagttagagc gcggcttgta ccacctttca acacgcgttc  30540
gacttcatca caaatgatac cagcgttcaa gttcgccatt agtcggtgaa ccatgctgaa  30600
```

```
accgtttgct agtcgagctg cttgtgacag gttctgagtt gtctggaatg cagcacttgt   30660
gtttgtcaag tcaaggttat cgtcagcgta tgtgtggatg tggcggtatc gtgcttcgtt   30720
ctggtacgca ccattcaaga tgctgtacag acgctcacga gagccagtat ccgcaacaac   30780
tgcgtcagcc ttacgtaaca gaccagtact tgctagacca cgtaatacac gagctaaacc   30840
gaactctttc attgcgatac taatgtcagt catctggtat aaaccggagt tctttagcat   30900
cacagtgtta gcgaggttgc ttgcaccacg catcagctca gggatgtcag taccgactgg   30960
gtagcctaac aggtggtcga ttgtgtcatc cactgctttg ccccattcct cagcaccctc   31020
tgccatacct agtcgagtct cagtgattga acggtcaagt gcacgtaaat cagtgatacc   31080
acgattcgca aacgccacgc gacctgacat acggtttgtg taaccttgca tcaagccaag   31140
tgtgttagtc tctaggatgt cagctagacg tagcacatca ccatcaatgt cgaactcttt   31200
gttcaagttc aagtcgagac ggttacgcaa gttcttcact ggtgcagtgc tgcctgtctt   31260
cggtacgttc acacgtagga actcattgat tttgtcgtct tcaacgccag catcacgcag   31320
agccatgaac aactcatcgt tatccatacc ttgcatcaag ttcttccatt gtgggccacc   31380
gttaccggat acaccattca caatgcggtt gtaccaagag tcagctacac gcgcagccag   31440
cttaccatcc atgttagtgt aagtgtcctg caacgcagag cgcagcagtt tcttaacttt   31500
aggtggttcg atgttacgca ctttctcata actgtattga cgagggatgt agtacttcga   31560
gcgtgggaac tcgtctgcac tgatagtacc ggatttcaca aggtgctcat gccaagactc   31620
agcccaaccg gaatcggtgt aggctttcac caaacgctca atgtcggctg gtggtgttgg   31680
gatttcacgc cctgctttct cagcactgta tgcttcatgc aggtacttag tcagcttatc   31740
ttcttccaca ctacgagctg tacgagcctt agcacggtta agaacatat caaaggtgtt   31800 aacgccatgc ttctcacgca tagcagccac aatcgcatcc tcgacagcag cagcacgtag   31860
gttctgctca agtgtcaagt tacgcttatg gtctaccaca ctggtagcac gctcacccat   31920
acgggtagca tcagatacaa gtaggttcgc taggtcttca ctaccacgag cgatgttatc   31980
ccagagcgcg aatgactgct tcaaagattt acggacacct tgctcaagac gtttagcacg   32040
ctcaaccgca gtagcaccac ggttcgcatc gtctgcaagg tcagccatac catcagagaa   32100
gaaagcgttc actttatcta ggttatcagc ttggtagtta gcaaccttaa caaaggcatc   32160
aaccgcttca tcaagagctg agcctgtgcc tttgaagcct aacattttca gaatcttctc   32220
agccacagct tgcaaagcat tctgacctgc acggacaccc ggtaacttcg ctaggtcttt   32280
caccatttcc ggtttagacg ccaactctgc taggaactca cgattgttag tcatagcgta   32340
gctgtactta cgggcgaact cacggttgtt tttcagtgag gcatgtaaag catcaaggtc   32400
acggatagcc tctgcaatct caggagcaac gttaccttta cttgcttgga ataaagtctt   32460
agatgtcgca gcatgaataa gctcatgcac agcaacgtct gcatctacgt ggttcaacat   32520
atcgcccacg gtcttgaaca ctgtaccgtc tttcgctgta gagcgcagtt tcagaaactc   32580
agtgttagca ccaaaggtgt aagatgagcg acgaccagta gcattcatta aacgcacttc   32640
cataccagag atagtatctg gcagtgcatc cataagagca cgagctgagt ctgacaaact   32700
atccatagta cggaggtgtg tcactaagtc ttgtgcttta atttgaactg tcttacgtcc   32760
ttgtcgagag gcaacaattc gaccccccaac aggtgtgtcc tgtaatggga aacttcgttc   32820 cccccttacct gtacgtggga ctttaccac ttctggcact tcatttacag gtgcgtcagg   32880
gtcaggcatt cgctgtacag caacctctgg ttttaccaca tcaggcacga tttctggagc   32940
```

-continued

```
gtcactcagc acgccaccag tctgtgcttt gcgtgctaaa cctgtctcag cggtgaacac   33000
atgctcagtt gcagaaccta aagcgcggct ctcaacctct gctgcattcg ctgctgcacg   33060
gacaccacga gttgcacgcg atacatcgta cagttggtca acaccaatta gacctgcggc   33120
aaccgctgtt acccactcag cctgacctag ttggtcttga gcgtagtaag tggttgctaa   33180
ctcaccagca cgcaatgcag cacgcacagc cataccagta cgaccaacca cacctgctgc   33240
acccataggg gcaaggagga acggtgcatc acctgctaag ttaccagcga tacctgcaaa   33300
catattctct gcttgcacac catcacgctt gcgttggtct tctacagcct ctttgcggta   33360
ctggtactca tcaaggctac gtgagccacc aatgaagttc aattcttctt ctgagtaccc   33420
tagaatgcgc agagaggtgt ctgctgtcat ggtagtgccg aggtcaaagg atgtgtcctc   33480
tgggaaatct ggcatcgttg ctttacgcac agccgcacct acgatgctgt taccaacacc   33540
tgctgcgaat gattcaagtc cagttgcttt cggtgtttcg aggcgtttaa ggtttgcctc   33600
acgctccgca gcgtttaaac ctaagtcggt agtgtcttcc catgccagcg caccagcgtc   33660
catgtctgcg ccgttcacgc ccttagcatt agactctaag ccagcaccct gtgaagatgg   33720
gcgacggttc tcaaaaatag ccatagtaat tcctcaaagc ataatgataa gggaggggca   33780
aatgccccac cacttagtaa taggttgggt acggattctt agcaggttgg ttctgttgaa   33840
gccaacttgt caagtcagta cgtaattgct cttgtcgagt cttcctgat tgtttgtacg   33900 caggggtctg catcatagcg ttcatcacta acatacggtt agttaggttg tcgaattggt   33960
tcacaccttt agcgtaatcc gccatagcct tagccacagg gttcgcgcta ccaccaccac   34020
cgtgatacgc aaggtcaacc agtacaggat acgcagcatc actcagctca agaccagcag   34080
acttagccgc tgacttaacc attgggatgt acgtgtcttc taggtcgccc ttgagcatac   34140
cgatagcttg tgggagtgtt acctcatcgg caatggcctt accggagtta gtgtgacgcc   34200
cgaagcctac agtctcacca ccacctgctt tcttcttctt gccaaggaag ccctcagatt   34260
ccatcaggtt agcggttaac ttaccgaaca cgaatgggtc gataccagac ttgttccacac   34320 cagtcacgtt cattgtcaca gcgcggttat tcgttgcgtc atagaacgta gcagcggtta   34380
ggccactttg ctgtgagcca agacctgcgg cagtcttaac ctcgtcgtcg tacattgtag   34440
ttgcagcctg ttgcagagtg cttcctgaga tactgtaacg ggtcacaata ccgtcggagt   34500
cttccacagc tacaaccata cccatagcgt caccacctgc tgcaccaatg tcaacagtca   34560
caccactcac atcggtctga atactagaca gcacagaagc cacttggttg ttcatggctt   34620
taacgaaagt ctcctgagag cctttgtatg agccgtagaa gtcgtctagc ttcttaccca   34680
caggaacgta cgtgtggatg ttgccaccgt tcacctgtag ctctacctga cgcgtacggg   34740
catctgcata agcagctttc tccatagcgc ccaagtcgtt agttagctct gggcgtttct   34800
gtgcaatgta cttccaactc tgtgccacag cagtagcacc agcagtcacc tgacggtcac   34860
tttctgtgcc gaagtcaagc cagttgttca gcttagtacc atcaatcaaa gcgttaggca   34920
tagtcgcatt ctgagcattg tacttaccag aggcgatagc ctgagcgttg cgtcgtaggt   34980
cgtcgaacag gatgttactc gcgttctcgg ggttctgcaa tgcagcattg cccattgggc   35040
cacgtaggtt ctccggtagg ttctgtagca tcgtctgctt accaatagca gtactcttgt   35100
cgtacatcat catccatgtg gcaacctgcg cctgttgttc ctcactgacg acgttatcct   35160
tgcctgtaaa gtcgattgtc gctaagactt gaccagtgtt agtactcata cgtttagccg   35220
ctagggacgc catgtatgaa tcgttagcct ttgaagcata cgccatcatt gccaagttac   35280
cttgagcagt gtctgggaag ttcttctcca gctctttacg agtcttgtct aagtccatac   35340
```

```
cgagctgacc agctaggaca gttgacggga tagcgttgtt cagtgcgagt tggaaagtgt    35400
tcgcttgacg cgctttcttc tccgcctcgt tcagacgctt cacatatgaa ccagcagtac    35460
ccgcctcgat aataccctgc tgtgccttgt cgtccacgaa gttacgtagt cgagttaact    35520
cagccgcttg ctcatccggt gatagtgctg ataggccgtt gatgtccgtt tcgaaactca    35580
ccatagcctg tgcagcttgt tggtttcctg cacggttgta ctcagtacgc aatgccttga    35640
taaccgtagg gcttagtaca cccatttcct tatcaaccac accttgtagc atgttgataa    35700
cacttggctc atcagtgcgc tgtgcaactg tctgtacgta cgctttggca cgttggattt    35760
tgtcatcctt tgacaagtgc gtagacaggt taatactgcg aagacctttc gcaatactcg    35820
cctgtgccat ttctggcgca cctgagtcca caaagctgta gaactctgct gctgtgccgt    35880
ctaggttgct gtctaacgca cggtcagcag ctacggtagc cattgcagcg gagtctttct    35940
ggaacttgtt acgagccgct acagacgttt cctgtaggtc ttgcaacagt gccattgccg    36000
attgcttagg gatatgtggg aggtacttac tcatctggct ggcgaacgca gcattgcgct    36060
cttggctcag cttgtcgaag tcctccaagt ccatccctg agatacggcg ttattgattt    36120
ggtcgatttg ctcctgacgg aacttgccca tttcctgatt cactgctgca ctcaagtagc    36180
ccgattggta ggactccttg aatagcatgt tcaccttgct gagcttttca tcttgcttgc    36240
tcatggcgtc agtcgtggca gtggcgtcta gcgcaccttg aattgctgca tctgctgcgg    36300
cttgattgta cgcacgttcc actgctggca cggctgtttg caggaatcca gcaatcagcg    36360
caccacttgc gtcaggctca gcctgtacgt tctccatacg tggagaggcc gcaccaatca    36420
acaggttgcc agttgcagct ccgagttgta gcggattgct ttggattggc atattatctc    36480
cttaccaact tgtagttatt ggtttatccg aataactgaa attaaggtca atttggttaa    36540
aggcactacg tccccaccaa tcgtaatcag cgtcattctt tcctacactt gggacttctt    36600
gtggctgtgt ctgactttgt ggtgttaact ggctgaaacc gtagttcgca gcagcgccca    36660
ccatgatacc agcagcctgt ccgtatgcag cgttcatgat ttgttcaccg gatgatgcca    36720
caccaccttg tagagcattg ctgccctcat cggtagtctt acgcaacatc atgttgaaac    36780
cctcgttcgt gattacatgc tggttctcaa ctgcaccttg agcacggtca gcgttgacca    36840
tgactgattg cgcagcgtca cgtgcactaa cgcccacagt gtccgtggca gcagccatag    36900
cacgtgtttg gttagcggca gcgttcttct gcgcattgat attgaatagc gcactagcgg    36960
tcttctggtt ctcaatagag cgttgcaagt taatctgcga cacagactga gctgtgctga    37020
gcatgacttt cttgttgtac tccatgatag cctgatttcg agctacggcg gctttgttct    37080
ccgccttagc tgcttgacta ccagtgaaca atgctgacgc cgcgcctact acagcaccga    37140
tagcagcacc ccaagggcca cctaccgatg caccctagc agcaccagac gcagcaccag    37200
tggcgacacc gccaccactt gcacctgcca tattaactcc ttatacgcga cgtcggcgtt    37260
ggttgtaacg aatgatatat tcaatttcca gaatgttcat atcctgtgta ccgtcagtac    37320
tcaagtacat ttcagtagac tgcgcattgc ttcggcacgg tacagggaca cgtgctaggt    37380
cagcaagtag cgccatatct ggctgaacgc tatcagtacc aaacacaagg ctagttgtgc    37440
tatctgagta atccaatccg atacttgggt caacgatacg tacatcgaac tcaccagtat    37500
ttcgagttgt taactcataa cgcaacagac gaaccggagc ggtactgatt aaggtatcgt    37560 tctggtctt cagcattgga ggtgtaggtg cgaacaggga ctcgtaccgg aaacctagat    37620
agatttcttc gtgagttgaa cccggctcaa cagtgaactc ccaagtgatt tcgtctacgt    37680
```

```
caatagccac ttcctcagag gcgcgtgcac cagtcgccac agcaccagtg agcttgccct   37740
cagctaccca aggacgcata tagattggca cgatacctttt accctcagtt gtaataggca   37800
cacggctcat tgcatctaag tgtggtaatc ggtcaacatc aaacgtcaca ccaccctgtt   37860
tagggtcgat ggtcgagata gtgattttgt cggtgctacc atcgtcatct gcggcaaaca   37920
acacaacacg gtcacgagca aagtgcagac tagcgacacg gtatgggaag aaccatttat   37980
gccatgcttg gtgtacttta ccttggttcg tgaagtgata ctcgtgtgca atcacttggc   38040
ggttgtcacc agtggttgcc attagtacga tgttcgcagc actcgcactc tgcatgaaac   38100
gagcctcacc ctcaatgtaa cgtgggatgt gcgtcgtaac gtcttgagac acgtactgcg   38160
acgatgtgta ctgtgagggt acaagctcca gaactgcact gaatgcttcg cttcgaggtg   38220
caggatacat cagggtctgt gaggttgtaa caggtgctac aaacgcatta caggccaaat   38280
ctgaggtcaa caccacgctt gcgttatcag gcgcgagtaa ctgttgcagg gatggtacta   38340
ccgcctgtgt actgtcacca agcagaatca agtccttatt gaactgcaac gcttggcgga   38400
acactgagtt ctgagccgaa ccggatgcaa tgtcaatacg gtctgttggg tcaagggaac   38460
tcacggtaga gcggaagaaa cggtctggtt cgccagtggc actcatacag acgtacgcac   38520
cagagagaag cactagacga ccttggaacg taccgatacc agtgatgcgg cgttcctcaa   38580
ggaatgtcgg tgcagggtta gttaagtcat cacctgcgag acgcccctcc atgatatgtt   38640
gctccacgtt gtcatcgaca atcttatagg gcacatccac gctaatagcg gtcacagagt   38700
tgtagtcacc agattccaac cacacaccct tttcggcact gtaacgatac cacacaagtg   38760
cacgctctga ttgacccaca gcacacaatg caccatcggc agacgggtgc agacgcgcag   38820
ggaggtcagt ctctaggttt acctgtgatt ggtttgagta gccaacgtaa ggtgagccag   38880
atgtacttgt gattttaagg tcagtacctg tgattaactc aaagtaaatg tacgggccaa   38940
cacgtacagc gaagtctaca ccaactgcaa tcagagcctc cacgagttta cgtgcaattg   39000
cttctggcac agattggtct gcgtcacctg ctgttgtacc gtctggtgtg gtgtacgtca   39060
cggtttggct accgagcgac cacacaacgg acaggtcgta ctctttactg aacgcaccac   39120
tcttgacgaa gtagaagcct gttgttttcg ggtctttctt gtcagagttg tcagtcgttg   39180
cagacgggcg cttctcagtg tttagaatgt acgtgatacc acccatactg gtagtctgga   39240
tactacggcg gtcagccgct aagaggtacg acaggttgcc ctcgttcacg atgttcttag   39300
cctctcggtc taagagccac cagccgccag tgttggtgtt gattactaag tgtcgtccgt   39360
cagcacctcg ttcgagatac tgcgtgtaca gtgcatcacc ctcaccaatc gggccaaaat   39420
cgtgcacact cacgaacagg ctaccgggac gacgacggat acctgttact gggtcggaca   39480
gcatgttaac ttgcgcagag cattgtcctg ccacacgttc gcgtggaatc tgttgggaca   39540 cacctttgcag caagtcattc aatgcaccct caaatggacg agccatgatt cacctctatg   39600
tatataatgc agagcggata cgacggtagc gccctgtctt gcttgtactg tatcggcggt   39660
tacgtaggtt ctgcttgtgt agcactcgga acgcctcttg cgcctgacgg tctaggttct   39720
ggtactggtt gtccacgcct aagtcatttg cgtacacttg catagccgct tcatacgcga   39780
ccacgtgttg agccatttct ggcaggtgtt caaacggtgt gtcaaacacg atgcgtagga   39840
acttggactc gtcgaatacg atgttattgg tggcgtaatc caacagtaag ccgttctcat   39900
cctcaccgta cattacatca ctagccgcat cataaatgtc aatggttgcg ctaggcaggt   39960
agatatgccc ctctacatca ggatacacgc tcatttcacg ctcgttaaac caccaaccat   40020
cgctcagcaa tagtttgcgt ttagtttcaa gagtgtcctt gacgatacca atggtagggt   40080
```

```
tgcgaacagt gtcggatgtg atgcggtact caccaatcgc agtcaacgag atattgattg   40140
catctagtaa ggtcatattt taagcactcc aaacaaaaaa ggggagcagc cgaagccact   40200
ccccttgggt attattgctg attagctctc agtctctgtt ttctctggcg caccagcagc   40260
tacaggtttg ttctgacgag cgtcacgctt ctgcttttga cgcgctgtgt ccggtgtcca   40320
cttagcgcgt aggtcgatta ctttagccat ttacttgctc cttatgctgc tggttcttcg   40380
aacttagtaa cgattgcagt gtctggacga cgctgaccaa ctgtgtacat agcgtaacag   40440
tcaagtacgt tacagaactc tttctcgtca tcccagatac gagttgtgaa tggatgtgct   40500
tccacagtca caagtgtacg agatttagag aaagtaacca tttgacattt cgcatcttcc   40560
gcagacacgt tgaacgaagt gccaagtggg tgagcagcga ttgcaccagt gggaactcg   40620
gtacactcaa ctactggtac accgttcata cgaacgacac gacgaccgcc gtagtcagac   40680
atatcaacgt tgaactcttg gttcagcagt tttggatgct ctactagcgc agagtaaatg   40740
tctggtgaca caagagtgat ttggtcagtc agtggaactt tacgtttcac cagctcagtc   40800
acaccagcct tgtgagcttc gttgatagag atagcgttcg cttcaagttc ttcttgagaa   40860
accgcagcag ccttgtaagt tgccagtact tccacaccat cattgaaagc aggtttcaag   40920
tggtcaggtg cgtcccaagt acgacccttg atgatttgga taaggtgcgc ttggtcaaag   40980
acctcagcga actcagagcc gttgttctga cccatttcgg ttaggaagtc aggtgcagtc   41040
cagtcgtctt ggtagtcgat tgggttacgg atgtacagca ctgtatccac gacgataatc   41100
attttatcgt tacgtacagg cgtgttatcc agagtttcac cggaacgacg gcctttcact   41160
gttgaagtgt tcaagcggtc aatacggtaa gtgttagagc gttcagcagt tgaacgttgt   41220
gcagacaagc cacggaacat agctgcgtac tggaaacgag tgtcaacttc gttttggtac   41280
acttctaggt ggatgtcttg gtcggaagca gcaccacccc aatgtgggcg agttagacct   41340
gctttgtatg aagtatcagc cattttgaat ccttatggtt gaaaagtttta aatctggagt   41400
ttcagacgcc agaaacgcaa aaaggggctt atcgccccag ttgtttgcca cgtgcgcggc   41460
gttcaagcag attctgatac gcttgaccag cagggccact ttcaaaagaa gtgttaccaa   41520
acttggtgcg taaatccgca agttctttcg agaactcagc agcagacaac gcagtgttgc   41580
cagcttgacc acccatccca tgaatgtgtt ggccttgagt tggtaaagca ccagactgac   41640
gggcgtagtc tagtaccatc tgagctgcgt ccttggctag accgctgttt gccatagtct   41700
tgaccgcagt ctgaatatgg gcaggagcgt tcgccatgaa cacatcacgc gcttgtgccc   41760
acgcctcagc accaccagct agagtgtgta cttcattaac agtgcgttca gtgtttgaag   41820
cagcgttagc gaggtacgtt tcagctaagg tctttgcgta gccagcgtag ttgccgaggc   41880
gttcttggag gaacttctcg tcaatcaaag aggcatcacc ataacgcagt gcattaccca   41940
tagctcgctc tacgtcagca tcggtacagc ccgatacttg agcaagcatc tgtaagccag   42000
catcaactgc ggcgtcacct gtctgtaatg taatctgacc tgcggctggg tctgtttgct   42060
ctggttcagc aggaacttga ggttctggct gtggagcagc agcaggttgt ggttgattac   42120
ccagtacagg gtcgtcggct ggtgcaggtt gtggtgcagg gttctgcgtt ggttgtggtt   42180
gattagggac gtcagcaggt ttacccgctg ttggtacgcc cggtggaaga tttgtatctt   42240
gcattattga gtcaatcctt gctgttcaga caatagtgca gcagagccag catcaagtgc   42300
cataccggag gcaggggctt gagcagcagc ttcctcagcc gcctgtagct gttgcagctc   42360
ttgttctgtg tagaaaatct cagacgggtc aacaccatga cctgcgagga ttaggtcaat   42420
```

```
cactcggtca gggttggtac gttttgtagc ttgtgcaagt acagggagaa tcaagttaat    42480
atcgttcgca actagaccta gacgttgcac cacaatacta cggttgatag ccgcagtacc    42540
tacttgaatg tctaggctaa ccgcattagc ttgcagcagt gccagcagct caggtcgagc    42600
ctcaactgtc aggatgtgcg ctaacgggat atgcagaatc tcagcaagag tagcgtagat    42660
gccacccatg ttttcttctg cttcacgaac gttgttcttg atttcttctg ctgttacacg    42720
ttcagcatca cggacgttac cagtgtacat gaacgctcgt gccagctccg caagaaccat    42780
ctgtaggtca ttcacgacct cagcaatctt gcgtgcctca ccagcttcat gcgccttgat    42840
accctcacca tcacctgcaa cgtactcacc agtctcagca tcattcaatg cgtcaacgtc    42900
agcagtactc ttaggcgaca cgaggttaac gactcgcatt gcttcaatct catacagagt    42960
cagtgcttga gttagctctg acacacgtgc gaacgcacct gcatggtctt ccacgtggcc    43020
acgaccataa tgctcaccag aaaccaagtt ccacaccgca gggatgtaag gacaaagctt    43080
ctcagggtaa acactaagtg tgccaacagg cttaccatca atctgttgag taatcacaaa    43140
aacgtcacca gcatcacgcg tctcgcgttg aatcttggtg tacaaccaaa catcagtggt    43200
agggtctgtg tatccggttg g                                              43221
```

VIBRIO PARAHAEMOLYTICUS BACTERIOPHAGE VIB-PAP-2 AND USE THEREOF FOR INHIBITING PROLIFERATION OF *VIBRIO PARAHAEMOLYTICUS*

CROSS-REFERENCE TO RELATED APPLICATIONS

This application is a U.S. National Phase Application of International Application No. PCT/KR2016/012905, filed Nov. 10, 2016, which claims priority to Korean Application No. 10-2015-0182592, filed Dec. 21, 2015, each of which are hereby incorporated by reference in their entirety.

REFERENCE TO SEQUENCE LISTING

The Sequence Listing submitted Jul. 6, 2018 as a text file named "08162_0043U1_Revised_Sequence_Listing.txt," created on Jun. 28, 2018, and having a size of 56,858 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills *Vibrio parahaemolyticus* cells, and a method for preventing and treating the infections of *Vibrio parahaemolyticus* using a composition comprising the bacteriophage as an active ingredient. More particularly, the present invention relates to a Podoviridae bacteriophage Vib-PAP-2 (Accession NO: KCTC 12910BP) that is isolated from the nature and can kill *Vibrio parahaemolyticus* cells specifically, which has a genome represented by the nucleotide sequence of SEQ. ID. NO: 1, and a method for preventing the infections of *Vibrio parahaemolyticus* and thereafter treating them using the composition comprising said bacteriophage as an active ingredient.

2. Description of the Related Art

*Vibrio parahaemolyticus* is a Gram-negative bacillus belonging to the genus *Vibrio* and gives rise to acute food poisoning and enteritis in human and vibriosis in fish. There are a variety of symptoms by the vibriosis in fish. The infected fish may manifest darkened body color and skin ulcer and sometimes reveal reddening of rostrum and skin flare. Also, in terms of anatomical signs, bleeding or congestion of liver is observed.

The outbreak of vibriosis caused by the infection of *Vibrio parahaemolyticus* occurs frequently, thereby results in economical damages a lot. Therefore, it is required to develop a novel procedure for preventing and further, treating the infections of *Vibrio parahaemolyticus*.

The fish aquaculture industry continues to develop rapidly every year, because it makes food resources acquired easily when being insufficient in the wild fish capture. However, as the aquaculture industry develops increasingly, environmental pollution caused by feeds increase around aquafarms. Particularly, a lot of antibiotics included in the feeds are spread widely to rather threaten human health. In the aquafarms, chemotherapeutic antibiotics are utilized in an excessive amount to eradicate bacterial diseases practically. As a consequence, multi-drugs resistant bacterial strains are emerging frequently, which leads to economical losses in the aquafarms. Moreover, such an abuse of antibiotics without any restraint can threaten national health and thereby influence mentally upon nations to reduce consumption of fish, resulting in weakening overall competition of the fish aquaculture industry. Therefore, it is urgently requested to develop a novel method for preventing bacterial infections and thereafter treating them effectively. Especially, the safety of sea food becomes a main social concern and thus, environmental-friendly methods are preferred.

Recently, the use of bacteriophages has drawn our attention as a new way of treating bacterial infections. Particularly, the reason of our high interest in bacteriophages is because bacteriophage-based treatment is a nature-friendly method. Bacteriophages are an extremely small microorganism that infects bacteria, which are called phage in short. Once bacteriophage infects bacteria, the bacteriophage is proliferated in the inside of the bacterial cell. After proliferation, the progenies destroy the bacterial cell wall to escape from the host, suggesting that the bacteriophage has the killing ability of bacteria. The bacteriophage infection is characterized by its high specificity, so that a certain bacteriophage infects only a specific bacterium. That is, the bacterium that can be infected by certain bacteriophage is limited, suggesting that bacteriophage can kill only a specific bacterium and cannot harm other bacteria. Due to this cell specificity, the bacteriophage confers antibacterial effects upon target bacteria and excludes commensal bacteria in environmental or the intestines of fish. Meanwhile, conventional antibiotics affect various kinds of bacteria coincidently. However, the use of bacteriophages does not disturb normal microflora either in the intestines of fish, because of killing the target bacteria selectively. Hence, the bacteriophage may be utilized safely and thus lessen the probability of adverse actions, compared to any other antibiotics.

Bacteriophage was first found out by an English bacteriologist Twort in 1915 when he noticed that Micrococcus colonies melted and became transparent by something unknown. In 1917, a French bacteriologist d'Herelle found out that *Shigella dysenteriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella typhi*, and *Vibrio cholerae* have been continuously identified.

Owing to the unique capability of bacteriophage to kill bacteria, bacteriophages have been studied and anticipated as a better method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new antibacterial agent that can replace the conventional antibiotics. Furthermore, the recent regulation of using antibiotics is fortified by the government world-widely. The interest on bacteriophages is increasing more and also industrial applications are increasingly achieved.

As demonstrated above, bacteriophages tend to be highly specific for bacteria. The specificity often makes bacteriophages effective upon a part of bacteria, even though belonging to the same kinds. In addition, the effectiveness of bacteriophage is different, depending upon target bacterial strains. Therefore, it is necessary to collect many kinds of bacteriophages that are useful to control specified bacteria efficiently. Hence, in order to develop a use of bacteriophages for coping with *Vibrio parahaemolyticus*, a lot of bacteriophages (many kinds of bacteriophages that give an antibacterial action against *Vibrio parahaemolyticus*) should be acquired. Furthermore, the resulting bacteriophages need to be screened whether or not superior to others in respects of antibacterial strength and spectrum.

Therefore, the present inventors tried to develop a composition applicable for the prevention or treatment of *Vibrio parahaemolyticus* infections by using a bacteriophage that is isolated from the nature and can kill *Vibrio parahaemolyticus* cells selectively, and further to establish a method for preventing or treating the infections of *Vibrio parahaemolyticus* using the composition. As a result, the present inventors isolated bacteriophages suitable for this purpose and secured the nucleotide sequence of the genome that distinguishes the bacteriophage of the present invention from other bacteriophages. Then, we have developed a composition comprising the isolated bacteriophage as an active ingredient, and confirmed that this composition could be efficiently used to prevent and treat the infections of *Vibrio parahaemolyticus*, leading to the completion of the present invention.

SUMMARY OF THE INVENTION

It is an object of the present invention to provide a Podoviridae bacteriophage Vib-PAP-2 (Accession NO: KCTC 12910BP) that is isolated from the nature and can kill *Vibrio parahaemolyticus* cells specifically, which has the genome represented by the nucleotide sequence of SEQ. ID. NO: 1.

It is another object of the present invention to provide a composition applicable for the prevention of *Vibrio parahaemolyticus* infections, which comprises the bacteriophage Vib-PAP-2 that can infect and kill *Vibrio parahaemolyticus* cells, as an active ingredient and a method for preventing the infections of *Vibrio parahaemolyticus* using said composition.

It is another object of the present invention to provide a composition applicable for the treatment of *Vibrio parahaemolyticus* infections, which comprises the bacteriophage Vib-PAP-2 that can infect and kill *Vibrio parahaemolyticus* cells, as an active ingredient and a method for treating the infections of *Vibrio parahaemolyticus* using said composition.

It is another object of the present invention to provide an immersion agent (medicine bath agent) for preventing and treating the infections of *Vibrio parahaemolyticus* using said composition.

It is also an object of the present invention to provide a feed additive effective upon farming by preventing and treating the infections of *Vibrio parahaemolyticus* using said composition.

To achieve the above objects, the present invention provides a Podoviridae bacteriophage Vib-PAP-2 (Accession NO: KCTC 12910BP) that is isolated from the nature and can kill specifically *Vibrio parahaemolyticus* cells, which has the genome represented by the nucleotide sequence of SEQ. ID. NO: 1, and a method for preventing and treating the infections of *Vibrio parahaemolyticus* using a composition comprising the bacteriophage as an active ingredient.

The bacteriophage Vib-PAP-2 has been isolated by the present inventors and then deposited under the Budapest Treaty on the International Procedure at Korean Collection for Type Cultures, Korea Research Institute of Bioscience and Biotechnology (KRIBB), 125 Gwahak-ro, Yuseong-gu, Daijeon 305-806, Republic of Korea; the deposit was made on Sep. 22, 2015 (Accession NO: KCTC 12910BP).

In addition, the present invention also provides an immersion agent and a feed additive applicable for the prevention or treatment of *Vibrio parahaemolyticus* infections, which comprises the bacteriophage Vib-PAP-2 as an active ingredient.

Since the bacteriophage Vib-PAP-2 included in the composition of the present invention kills *Vibrio parahaemolyticus* cells efficiently, it is regarded effective to prevent or treat vibriosis (infections) caused by *Vibrio parahaemolyticus*. Therefore, the composition of the present invention can be utilized for the prevention and treatment of vibriosis caused by *Vibrio parahaemolyticus*, but not limited thereto.

In this description, the term "prevention" or "prevent" indicates (i) to block the infections of *Vibrio parahaemolyticus*; and (ii) to block the development of diseases caused by *Vibrio parahaemolyticus*.

In this description, the term "treatment" or "treat" indicates (i) to suppress the vibriosis caused by *Vibrio parahaemolyticus*; and (ii) to relieve the virbiosis caused by *Vibrio parahaemolyticus*.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

The pharmaceutically acceptable carrier included in the composition of the present invention is the one that is generally used for the preparation of a pharmaceutical formulation, which is exemplified by lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the present invention can additionally include lubricants, wetting agents, sweeteners, flavors, emulsifiers, suspending agents, and preservatives, in addition to the above ingredients.

In the composition of the present invention, the bacteriophage Vib-PAP-2 is included as an active ingredient. At this time, the bacteriophage Vib-PAP-2 is included at the concentration of $1 \times 10^1$ pfu/ml~$1 \times 10^{30}$ pfu/ml or $1 \times 10^1$ pfu/g~$1 \times 10^{30}$ pfu/g, and preferably at the concentration of $1 \times 10^4$ pfu/ml~$1 \times 10^{15}$ pfu/ml or $1 \times 10^4$ pfu/g~$1 \times 10^{15}$ pfu/g.

The composition of the present invention can be formulated by the methods that can be performed by those in the art by using a pharmaceutically acceptable carriers and/or excipients in the form of unit dose or in a multi-dose container. The formulation can be in the form of solution, suspension or emulsion in oil or water-soluble medium, extract, powder, granule, tablet or capsule. At this time, a dispersing agent or stabilizer can be additionally included.

The composition of the present invention can be prepared as an immersion agent or a feed additive according to the purpose of use, but not always limited thereto.

For this purpose, other bacteriophages that can confer an antibacterial activity against other bacterial species can be further comprised in the composition of the present invention in order to improve its effectiveness.

In addition, other kinds of bacteriophages that have an antibacterial activity against *Vibrio parahaemolyticus* can be further comprised in the composition of the present invention. Besides, these bacteriophages can be combined properly so as to maximize antibacterial effects, because their antibacterial activities against *Vibrio parahaemolyticus* can be differential in respects of antibacterial strength and spectrum.

ADVANTAGEOUS EFFECT

The method for preventing and treating the infections of *Vibrio parahaemolyticus* using this composition comprising the bacteriophage Vib-PAP-2 as an active ingredient, has the advantage of high specificity for *Vibrio parahaemolyticus*, compared with the conventional methods based on the chemical materials including the conventional antibiotics. That means, the composition of the present invention can be used for preventing or treating the infections of *Vibrio parahaemolyticus* specifically without affecting normal microflora, and accordingly has fewer side effects. In general, when chemical materials such as antibiotics are used, commensal bacteria are also damaged to weaken immunity in animals with carrying various side effects. In the meantime, the composition of the present invention uses the bacteriophage isolated from the nature as an active ingredient, so that it is very nature-friendly.

Besides, the antibacterial activity of bacteriophages against target bacteria is different, even if belonging to the same species, in respects of antibacterial strength and spectrum (within several strains of *Vibrio parahaemolyticus*, the antibacterial range of bacteriophages contributing to every strain. Typically, bacteriophages are usually effective upon a part of bacterial strains even in the same species. That is to say, the antibacterial activity of bacteriophage is different depending on bacterial strain in spite of belonging to the same species). Then, the bacteriophage of the present invention can provide antibiotic activity against *Vibrio parahaemolyticus* different to that provided by other bacteriophages acting on *Vibrio parahaemolyticus*. Therefore, the bacteriophage of the present invention can provide different applicability for fish aquaculture industry.

BRIEF DESCRIPTION OF THE DRAWINGS

The application of the preferred embodiments of the present invention is best understood with reference to the accompanying drawings, wherein:

FIG. 1 is an electron micrograph showing the morphology of the bacteriophage Vib-PAP-2.

FIG. 2 is a photograph illustrating the capability of the bacteriophage Vib-PAP-2 to kill *Vibrio parahaemolyticus* cells. The clear zone on the dish is the formation of plaque by lysis of target bacteria cells.

DESCRIPTION OF THE PREFERRED EMBODIMENTS

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation of Bacteriophage Capable of Killing *Vibrio Parahaemolyticus*

Samples were collected from the nature to screen the bacteriophage capable of killing *Vibrio parahaemolyticus*.

In the meantime, the *Vibrio parahaemolyticus* strain used for the bacteriophage isolation herein was obtained from Korean Collection of Type Cultures, Korea Research Institute of Bioscience and Biotechnology (Accession NO: KCTC 2729).

The isolation procedure of the bacteriophage is described in detail hereinafter. The collected sample was added to LB (Luria-Bertani; tryptone, 10 g/L; yeast extract, 5 g/L; sodium chloride, 10 g/L) broth inoculated with *Vibrio parahaemolyticus* at the ratio of 1/1,000, followed by shaking culture at 37° C. for 3~4 hours. Upon completion of the culture, centrifugation was performed at 8,000 rpm for 20 minutes and supernatant was recovered. The recovered supernatant was inoculated with *Vibrio parahaemolyticus* at the ratio of 1/1,000, followed by shaking culture at 37° C. for 3~4 hours. When the sample contained the bacteriophage, the above procedure was repeated total 5 times in order to increase the titer of the bacteriophage. After repeating the procedure 5 times, the culture solution proceeded to centrifugation at 8,000 rpm for 20 minutes and the resulting supernatant was recovered. The recovered supernatant was filtrated by using a 0.45 μm filter. The obtained filtrate was used in spot assay for examining whether or not the bacteriophage capable of killing *Vibrio parahaemolyticus* was included therein.

Spot assay was performed as follows; LB broth was inoculated with *Vibrio parahaemolyticus* at the ratio of 1/1,000, followed by shaking culture at 37° C. for overnight. 3 ml (1.5 of $OD_{600}$) of the culture broth of *Vibrio parahaemolyticus* prepared above was spread on LA (Luria-Bertani Agar; tryptone, 10 g/L; yeast extract, 5 g/L; sodium chloride, 10 g/L; agar, 15 g/L) plate. The plate stood in a chamber for about 30 minutes to dry. After drying, 10 μl of the resulting filtrate was spotted directly onto the surface of the *Vibrio parahaemolyticus* lawns and dried for about 30 minutes. Following drying, the plate was incubated at 37° C. for a day and then, examined for the formation of clear zone on the surface of the bacterial lawns. If a clear zone was generated where the filtrate was dropped, it is judged that the bacteriophage capable of killing *Vibrio parahaemolyticus* should be included in the filtrate. Through the above procedure, the filtrate containing the bacteriophage having the killing ability of *Vibrio parahaemolyticus* can be obtained.

After that, the bacteriophage was isolated from the filtrate confirmed above to have the bacteriophage capable of killing *Vibrio parahaemolyticus*. The conventional plaque assay was used for the isolation of pure bacteriophage. In detail, a plaque formed in the course of the plaque assay was picked up by using a sterilized tip, which was then added to the culture solution of *Vibrio parahaemolyticus*, followed by culturing at 37° C. for 4~5 hours. Upon completion of the culture, centrifugation was performed at 8,000 rpm for 20 minutes to obtain supernatant. The recovered supernatant was inoculated with *Vibrio parahaemolyticus* culture at the ratio of 1/50, followed by culturing at 37° C. for 4~5 hours. To increase the titer of the bacteriophage, the above procedure was repeated at least 5 times. Then, centrifugation was performed at 8,000 rpm for 20 minutes to obtain supernatant. Plaque assay was performed by using the resulting supernatant. In general, the pure bacteriophage isolation is not completed by one-time procedure, so the above procedure was repeated by using the resulting plaque formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by electron microscopy. Until the pure bacteriophage isolation was confirmed by electron microscopy, the above procedure was repeated. The electron microscopy was performed by the conventional method. Briefly, the solution containing the pure bacteriophage was loaded on copper grid, followed by negative staining with 2% uranyl acetate. After drying thereof, the morphology was observed using a transmission electron microscope. The electron micrograph of the bacteriophage isolated in the present invention is presented in FIG. 1. Based on the morphological characteristics, the bacteriophage isolated above was confirmed as belonging to the family Podoviridae.

The solution containing the pure bacteriophage confirmed above proceeded to purification. The culture broth of *Vibrio parahaemolyticus* was added to the solution containing the pure bacteriophage at the volume of 1/50 of the total volume of the bacteriophage solution, followed by culturing again for 4~5 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 ml of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was suspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Vib-PAP-2 and then deposited at Korean Collection for Type Cultures, Korea Research Institute of Bioscience and Biotechnology in Sep. 22, 2015 (Accession NO: KCTC 12910BP).

Example 2

Separation and Sequence Analysis of the Bacteriophage Vib-PAP-2 Genome

The genome of the bacteriophage Vib-PAP-2 was separated as follows. The genome was separated from the bacteriophage suspension obtained in Example 1. First, in order to eliminate DNA and RNA of *Vibrio parahaemolyticus* cells included in the suspension, DNase I and RNase A were added 200 U each to 10 ml of the bacteriophage suspension, which was incubated at 37° C. for 30 minutes. 30 minutes later, to remove the DNase I and RNase A activity, 500 μl of 0.5 M ethylenediaminetetraacetic acid (EDTA) was added thereto, which was incubated for 10 minutes. The suspension was further incubated at 65° C. for 10 minutes and then added with 100 μl of proteinase K (20 mg/ml) to break the outer wall of the bacteriophage, followed by incubation at 37° C. for 20 minutes. After that, 500 μl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the bacteriophage Vib-PAP-2 genome.

The nucleotide sequence of the bacteriophage Vib-PAP-2 genome obtained above was determined by Next Generation Sequencing analysis using Roche 454 GS Junior device. As a result, it is suggested that the final genome of bacteriophage Vib-PAP-2 has 43,221 bp of size and the nucleotide sequence of the whole genome has SEQ. ID. NO: 1.

Similarity of the genomic sequence of the bacteriophage Vib-PAP-2 obtained above with the previously reported bacteriophage genome sequences was investigated by using BLAST. From the BLAST result, it is demonstrated that the genomic sequence of bacteriophage Vib-PAP-2 has a relatively high homology with the genomic sequence of Vibrio bacteriophage VP93 (Genbank Accession NO: FJ896200.1) (Query coverage/identity: 95%/94%). Nevertheless, the bacteriophage Vib-PAP-2 has a circular genome while the Vibrio bacteriophage VP93 has a linear genome. Thus, it is determined that they should be different kinds of bacteriophages. In addition, the genomic sequence of bacteriophage Vib-PAP-2 was compared to that of Vibrio bacteriophage VP93 by using NEBcutter V2.0 Web program. As a result, it is illustrated that the bacteriophage Vib-PAP-2 genome can be digested in a single cut by 8 kinds of restriction enzymes (AhdI, BglI, BsaI, BseYI, BssHII, EarI, MscI, PsiI), while the Vibrio bacteriophage VP93 can be singly cut by 10 kinds (AcuI, AfeI, BmtI, BseRI, BssHII, EarI, MscI, NheI, NsiI, PflMI). Therefore, it is clarified again that they should be different kinds of bacteriophages.

Based upon this result, it is concluded that the bacteriophage Vib-PAP-2 should be a novel bacteriophage not reported previously. Either, it is referred that when bacteriophages are different in their kinds, their antibacterial strength and spectrum become different typically. As a consequence, it is confirmed that the bacteriophage Vib-PAP-2 provides have more remarkable antibacterial activity than any other bacteriophages aforementioned.

Example 3

Investigation of Killing Ability of the Bacteriophage Vib-PAP-2 Against *Vibrio Parahaemolyticus*

The killing ability of the isolated bacteriophage Vib-PAP-2 against *Vibrio parahaemolyticus* was investigated. To do so, the formation of clear zone was observed by the spot assay by the same manner as described in Example 1. The *Vibrio parahaemolyticus* used for this investigation were total 14 strains which had been isolated and identified as *Vibrio parahaemolyticus* previously by the present inventors. The bacteriophage Vib-PAP-2 demonstrated the killing ability against 13 strains of *Vibrio parahaemolyticus* used in this experiment. The representative result of the killing ability test is shown in FIG. 2. In the meantime, the activity of the bacteriophage Vib-PAP-2 to kill *Edwardsiella tarda, Vibrio anguillarum, Vibrio ichthyoenteri, Lactococcus garvieae, Streptococcus parauberis, Streptococcus iniae* and *Aeromonas salmonicida* was also investigated respectively. As a result, it is concluded that the bacteriophage Vib-PAP-2 does not have the killing activity against these microorganisms.

Therefore, it is confirmed that the bacteriophage Vib-PAP-2 has the specific ability to kill *Vibrio parahaemolyticus* cells and a broad antibacterial spectrum against *Vibrio parahaemolyticus*, suggesting that the bacteriophage Vib-PAP-2 of the present invention can be used as an active ingredient of the composition for preventing and treating the infections of *Vibrio parahaemolyticus*.

Example 4

Preventive Effect of Bacteriophage Vib-PAP-2 on the Infections of *Vibrio Parahaemolyticus*

100 μl of the bacteriophage Vib-PAP-2 solution at $1 \times 10^8$ pfu/ml was added to a tube containing 9 ml of LB broth. To another tube containing 9 ml of LB broth, the same amount of LB broth was further added. *Vibrio parahaemolyticus* culture solution was added to each tube until $OD_{600}$ reached about 0.5. Then, the tubes were transferred to a 37° C. incubator, followed by shaking-culture, during which the growth of *Vibrio parahaemolyticus* was observed. As presented in Table 1, the growth of *Vibrio parahaemolyticus* was inhibited in the tube adding the bacteriophage Vib-PAP-2 solution, while the growth of *Vibrio parahaemolyticus* was not inhibited in the tube without adding the bacteriophage solution.

TABLE 1

Growth inhibition of *Vibrio parahaemolyticus*

| Treatment | $OD_{600}$ | | |
|---|---|---|---|
| | 0 min. | 60 min. | 120 min. |
| −bacteriophage solution | 0.52 | 0.92 | 1.84 |
| +bacteriophage solution | 0.53 | 0.31 | 0.15 |

The above results indicate that the bacteriophage Vib-PAP-2 should not only inhibit the growth of *Vibrio parahaemolyticus* but also can kill *Vibrio parahaemolyticus*. Therefore, it is concluded that the bacteriophage Vib-PAP-2 can be used as an active ingredient of the composition in order to prevent the infections of *Vibrio parahaemolyticus*.

Example 5

Preventive Effect of Bacteriophage Vib-PAP-2 on the Infections of *Vibrio Parahaemolyticus* in Animal Model Preventive effect of the bacteriophage Vib-PAP-2 on sea basses suffered from *Vibrio parahaemolyticus* infection was investigated. Particularly, total 2 groups of juvenile sea bass (50 juvenile sea basses per group; body weight 5~7 g, body length 8~10 cm) were prepared, which were cultured separately in different water tanks for 14 days. Surrounding environment of the water tanks was controlled. The temperature and humidity in the laboratory where the water tanks stayed were also controlled. From the 1$^{st}$ day of the experiment, sea basses of the experimental groups (adding the bacteriophage) were fed with feeds adding the bacteriophage Vib-PAP-2 at $1 \times 10^8$ pfu/g according to the conventional feed supply procedure, while sea basses of the control group (without adding the bacteriophage) were fed with the same feed without adding the bacteriophage according to the conventional procedure. From the 7$^{th}$ day of the experiment, the feeds of both groups were contaminated with *Vibrio parahaemolyticus* at $1 \times 10^8$ pfu/g for 2 days and thereafter provided respectively twice a day so as to bring about the infections of *Vibrio parahaemolyticus*. From the next day of inducing such an infection for 2 days (the 9$^{th}$ day of the experiment), the feeds without contaminated *Vibrio parahaemolyticus* were provided again respectively for both the groups. Then, all the test animals were examined whether being suffered from *Vibrio parahaemolyticus* infection or not. The outbreak of infectious disease caused by *Vibrio parahaemolyticus* was detected by measuring a body darkening index. The measurement of body darkening index was performed by the conventional method obtaining Dark Coloration (DC) score (0: normal, 1: light coloration, 2: dark coloration). The results are shown in Table 2.

TABLE 2

| | Dark coloration score (average values) | | | | | |
|---|---|---|---|---|---|---|
| Days | D 9 | D 10 | D 11 | D 12 | D 13 | D 14 |
| Control group (−bacteriophage) | 0.68 | 0.72 | 0.76 | 0.92 | 1.08 | 1.20 |
| Experimental group (+bacteriophage) | 0.16 | 0 | 0 | 0 | 0 | 0. |

From the above results, it is confirmed that the bacteriophage Vib-PAP-2 of the present invention could be very effective to prevent infectious diseases caused by *Vibrio parahaemolyticus*.

Example 6

Therapeutic Effect of Bacteriophage Vib-PAP-2 on the Infections of *Vibrio Parahaemolyticus*

Therapeutic effect of the bacteriophage Vib-PAP-2 on sea basses suffered from *Vibrio parahaemolyticus* infection was investigated. Particularly, total 2 groups of juvenile sea bass (60 juvenile sea basses per group; body weight 5~7 g, body length 8~10 cm) were prepared, which were cultured separately in different water tanks for 14 days. Surrounding environment of the water tanks was controlled. The temperature and humidity in the laboratory where the water tanks stayed were also controlled. From the 5$^{th}$ day of the experiment, feeds adding *Vibrio parahaemolyticus* cells at $1 \times 10^8$ cfu/g were provided twice a day for 3 days according to the conventional feed supply procedure. Sea bass subjects showing clinical symptoms of infectious disease caused by *Vibrio parahaemolyticus* from the last day of this procedure, were observed in both water tanks. From the next day of providing feeds adding *Vibrio parahaemolyticus* cells for 3 days (the 8$^{th}$ day of the experiment), sea basses of the experimental groups (adding the bacteriophage) were fed with feeds adding the bacteriophage Vib-PAP-2 at $1 \times 10^8$ pfu/g according to the conventional feed supply procedure, while sea basses of the control group (without the bacteriophage) were fed with the same feeds without adding the bacteriophage Vib-PAP-2 according to the conventional procedure. After the 8$^{th}$ day of the experiment, all the test animals were examined whether being suffered from infectious disease caused by *Vibrio parahaemolyticus* or not. The outbreak of infectious disease caused by *Vibrio parahaemolyticus* was detected by measuring body darkening index. The measurement of body darkening index was performed by the conventional method obtaining Dark Coloration (DC) score (0: normal, 1: light coloration, 2: dark coloration). The results are shown in Table 3.

TABLE 3

| Days | \multicolumn{7}{c}{Dark coloration score (average values)} |
|---|---|---|---|---|---|---|---|

| Days | D 8 | D 9 | D 10 | D 11 | D 12 | D 13 | D 14 |
|---|---|---|---|---|---|---|---|
| Control group (−bacteriophage) | 0.93 | 1.00 | 1.07 | 1.13 | 1.23 | 1.37 | 1.40 |
| Experimental group (+bacteriophage) | 0.87 | 0.80 | 0.77 | 0.63 | 0.40 | 0.23 | 0.20 |

From the above results, it is confirmed that the bacteriophage Vib-PAP-2 of the present invention could be very effective to treat the infectious disease caused by *Vibrio parahaemolyticus*.

Example 7

Preparation of Feed Additives and Feeds

Feed additives were prepared by adding the bacteriophage Vib-PAP-2 solution at the concentration of $1 \times 10^8$ pfu/g feed additives. The preparation method thereof was as follows: Maltodextrin (50%, w/v) was added to the bacteriophage solution, mixed and then resulting mixture was freeze-dried. Lastly, the dried mixture was grinded into fine powders. The drying procedure above can be replaced with drying under a reduced pressure, drying at warm temperature, or drying at room temperature. To prepare the control for comparison, feed additives that did not contain the bacteriophage but contained only buffer (10 mM Tris-HCl, 10 mM MgSO$_4$, 0.1% Gelatin, pH 8.0) were prepared.

The above two kinds of feed additives were mixed with raw fish-based moist pellet at the volume of 250 times the volume of additives, resulting in two kinds of final feed additives.

Example 8

Preparation of an Immersion Agent (Medicine Bath Agent)

An immersion agent comprising $1 \times 10^8$ pfu/ml of bacteriophage Vib-PAP-2 was prepared. The preparation method was as follows: $1 \times 10^8$ pfu of the bacteriophage Vib-PAP-2 was added to 1 ml of buffer, which was well mixed. To prepare the control, the buffer itself that is the same with the one used for the mixture of the bacteriophage solution was prepared.

The prepared two kinds of immersion agents were diluted with water at the ratio of 1:1,000, resulting in the final immersion agents for the experiment.

Example 9

Effect on Sea Bass Aquafarming

The effect of the feeds and the immersion agents prepared in Example 7 and Example 8 on sea bass aquafarming was investigated. Particularly, the investigation was focused on the mortality. Total 500 juvenile sea basses (body weight 5~7 g, body length 8~10 cm) were grouped into two, 250 sea basses for each group, which proceeded to the following experiment (group A; fed with feed, group B; treated with immersion agent). Each group was divided to two sub-groups again, group of 125 sea basses each (sub-group—①: treated with the bacteriophage Vib-PAP-2, sub-group—②: not-treated with the bacteriophage Vib-PAP-2). Each sub-group sea bass were aquacultured in separate water tanks placed at a certain space interval. Each sub-group was distinguished and named as shown in Table 4.

TABLE 4

Sub-groups of sea bass in aquafarming experiment

| Treatment | Treated with the bacteriophage Vib-PAP-2 | Not-treated with the bacteriophage |
|---|---|---|
| Fed with feed | A-① | A-② |
| Treated with immersion agent | B-① | B-② |

Feeds were provided according to the conventional feed supply procedure as presented in Table 4 with the feeds prepared as described in Example 7. The treatment of immersion agent was also performed by the conventional procedure as presented in Table 4 with the immersion agent prepared as described in Example 8. The test result is shown in Table 5.

TABLE 5

Mortality of sea bass in aquafarming

| Group | Dead fish/total test fish (No.) | Mortality (%) |
|---|---|---|
| A-① | 3/125 | 2.4 |
| A-② | 25/125 | 20.0 |
| B-① | 8/125 | 6.4 |
| B-② | 32/125 | 25.6 |

The above results indicate that the feeds prepared by the present invention and the immersion agent prepared according to the present invention are effective to reduce the mortality of the cultured sea basses. Therefore, it is concluded that the composition of the present invention could be efficiently applied to improve outcomes of sea bass aquaculture.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating or decreasing the probability for developing an infection of *Vibrio parahaemolyticus*, which comprises a step of administering to a subject a composition comprising the Podoviridae bacteriophage Vib-PAP-2 (Accession NO: KCTC 12910BP) that can kill *Vibrio parahaemolyticus* cells specifically, wherein the Podoviridae bacteriophage Vib-PAP-2 comprises a genome represented by the nucleotide sequence of SEQ. ID. NO: 1, as an active ingredient.

2. The method for treating or decreasing the probability for developing an infection of *Vibrio parahaemolyticus* according to claim 1, wherein said composition is administered to a subject in the form of an immersion agent or a feed additive.

* * * * *